US010912791B2

(12) United States Patent
Hsia et al.

(10) Patent No.: US 10,912,791 B2
(45) Date of Patent: Feb. 9, 2021

(54) COMPOSITIONS COMPRISING ANTISENSE-ENCODED ERYTHROPOIETIN RECEPTOR AND USE THEREOF

(71) Applicant: The Board of Regents of the University of Texas System, Austin, TX (US)

(72) Inventors: Connie Hsia, Dallas, TX (US); Orson W. Moe, Dallas, TX (US); Kytai Nguyen, Grand Prairie, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 0 days.

(21) Appl. No.: 16/333,046

(22) PCT Filed: Sep. 11, 2017

(86) PCT No.: PCT/US2017/050911
§ 371 (c)(1),
(2) Date: Mar. 13, 2019

(87) PCT Pub. No.: WO2018/052835
PCT Pub. Date: Mar. 22, 2018

(65) Prior Publication Data
US 2019/0262376 A1 Aug. 29, 2019

Related U.S. Application Data

(60) Provisional application No. 62/394,474, filed on Sep. 14, 2016.

(51) Int. Cl.
| | | |
|---|---|---|
| *A61K 31/711* | (2006.01) | |
| *A61P 11/00* | (2006.01) | |
| *A61K 9/00* | (2006.01) | |
| *A61K 9/51* | (2006.01) | |
| *C12N 15/113* | (2010.01) | |
| *C07K 14/715* | (2006.01) | |
| *C12N 15/88* | (2006.01) | |

(52) U.S. Cl.
CPC ............ *A61K 31/711* (2013.01); *A61K 9/007* (2013.01); *A61K 9/0019* (2013.01); *A61K 9/0053* (2013.01); *A61K 9/5153* (2013.01); *A61K 9/5161* (2013.01); *A61P 11/00* (2018.01); *C07K 14/715* (2013.01); *C12N 15/113* (2013.01); *C12N 15/88* (2013.01); *C12N 2310/11* (2013.01)

(58) Field of Classification Search
CPC ....... C12N 15/113; C12N 15/88; A61K 31/71
See application file for complete search history.

(56) References Cited

U.S. PATENT DOCUMENTS

2010/0015050 A1* 1/2010 Panyam ................. B82Y 5/00
514/1.1
2011/0195030 A1* 8/2011 Mumper ............ A61K 49/1809
424/9.32
2015/0064236 A1* 3/2015 Bancel .................... C12P 21/00
435/226

FOREIGN PATENT DOCUMENTS

| WO | WO 2017-008016 | 1/1917 |
|---|---|---|
| WO | WO 2010-065792 | 6/2010 |
| WO | WO 2015-189813 | 12/2015 |

OTHER PUBLICATIONS

Ravikumar et al. Nanomedicine: Nanotechnology, Biology, and Medicine 12, published Oct. 27 2015 on-line, 811-821 (Year: 2016).*
Zhang et al. PNAS vol. 105, pp. 7612-7617 (Year: 2008).*
Addgene.org, Vector Database: Plasmid: p3cFLAG-CMV-14. Webpage [online]. Oct. 7, 2015 [date verified by web.archive.org; retrieved on Oct. 25, 2017]. Retrieved from the Internet: <URL: http://www.addgene.org/vector-database/1621/>; p. 1.
Brines, et al., "Discovering erythropoietin's extra-hematopoietic functions: biology and clinical promise." *Kidney international* 70.2 (2006): 246-250.
Foster, et al., "Upregulation of erythropoietin receptor during postnatal and postpneumonectomy lung growth." *American Journal of Physiology—Lung Cellular and Molecular Physiology* 287.6 (2004): L1107-L1115.
Heitrich et al., "Erythropoietin attenuates renal and pulmonary injury in polymicrobial induced-sepsis through EPO-R, VEGF and VEGF-R2 modulation," *Biomedicine & Pharmacotherapy*, 82:606-613, 2016.
Hu, et al. "Engineering the lipid layer of lipid—PLGA hybrid nanoparticles for enhanced in vitro cellular uptake and improved stability." *Acta Biomaterialia* 28 (2015): 149-159.
Hu, et al. "Erythropoietin promotes the protective properties of transplanted endothelial progenitor cells against acute lung injury via PI3K/Akt pathway." *Shock* 42.4 (2014): 327-336.
Ikarashi et al., "Erythropoietin, but not asialoerythropoietin or carbamyl-erythropoietin, attenuates monocrotaline-induced pulmonary hypertension in rats," *Clinical Experimental Heypertension*, 34(8):575-581, 2012.
Liu, et al. "hSWS1• SWSAP1 is an evolutionarily conserved complex required for efficient homologous recombination repair." *Journal of Biological Chemistry* 286.48 (2011): 41758-41766.
MacRedmond et al., "Erythropoietin inhibits respiratory epithelial cell apoptosis in a model of acute lung injury." *Eur Respir J.*, 33 :1403-1414, 2009.
Moe, "Generation of high impact resources for erythropoietin receptor research," *National Institutes of Health*, 2015.
PCT International Preliminary Report on Patentability issued in International Application PCT/2017/050911, dated Mar. 28, 2019.
PCT International Search Report and Written Opinion issued in International Application PCT/2017/050911, dated Dec. 12, 2017.

(Continued)

*Primary Examiner* — Brian Whiteman
(74) *Attorney, Agent, or Firm* — Parker Highlander PLLC

(57) ABSTRACT

Provided herein are nanoparticles comprising antisense-encoded erythropoietin receptor (RopE) alone or in combination with erythropoietin receptor (EpoR). Also provided herein are methods of treating or preventing lungs disorders comprising administering RopE alone or in combination with EpoR.

21 Claims, 29 Drawing Sheets

Specification includes a Sequence Listing.

(56) References Cited

OTHER PUBLICATIONS

Punnakitikashem et al., "Abstract 28: Extracellular matrix coating enhances nanoparticle uptake by lung epithelial cells," *Circulation Research*, 117:A28, 2015.

Ravikumar et al., "Lung protection by inhalational delivery of nanoparticle-encapsulated erythropoietin receptor CDNA," *American Thoracic Society Conference*, Denver, CO, Abstract, May 2015.

Ravikumar, et al. "Nanoparticle facilitated inhalational delivery of erythropoietin receptor cDNA protects against hyperoxic lung injury." *Nanomedicine: Nanotechnology, Biology and Medicine* 12.3 (2016): 811-821.

Wu, et al. "Selective targeting of alveolar type II respiratory epithelial cells by anti-surfactant protein-C antibody-conjugated lipoplexes," *Journal of Controlled Release* 203 (2015): 140-149.

Zhang, et al. "Synergistic upregulation of erythropoietin receptor (EPO-R) expression by sense and antisense EPO-R transcripts in the canine lung." *Proceedings of the National Academy of Sciences* 105.21 (2008): 7612-7617.

* cited by examiner

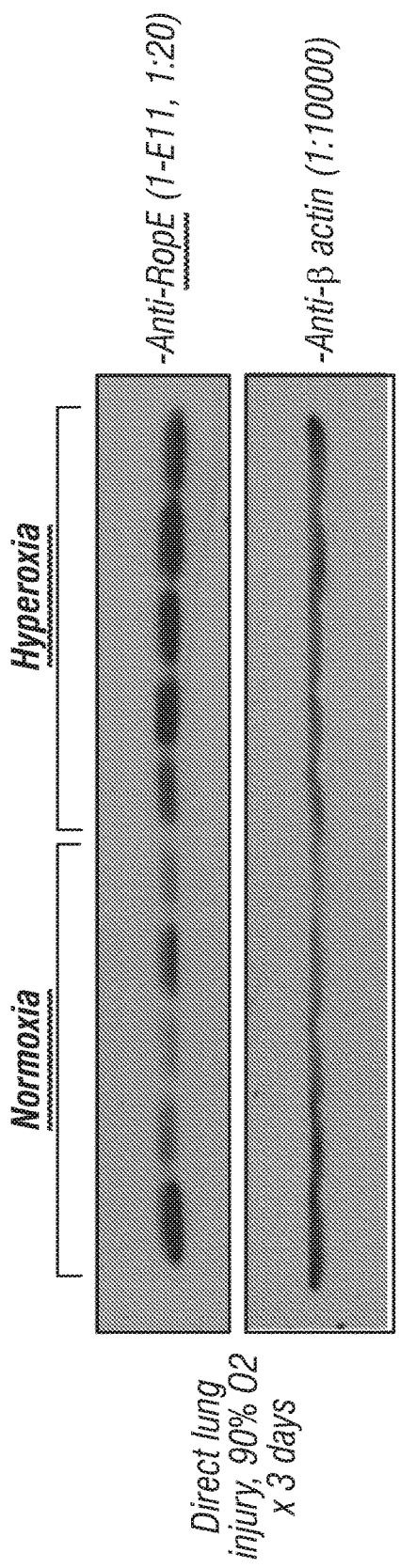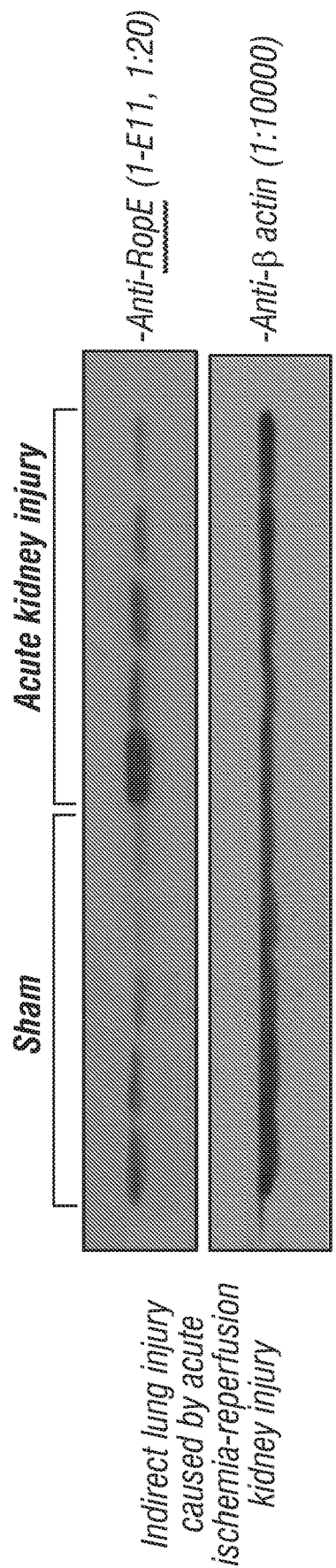
FIG. 3B
FIG. 3C

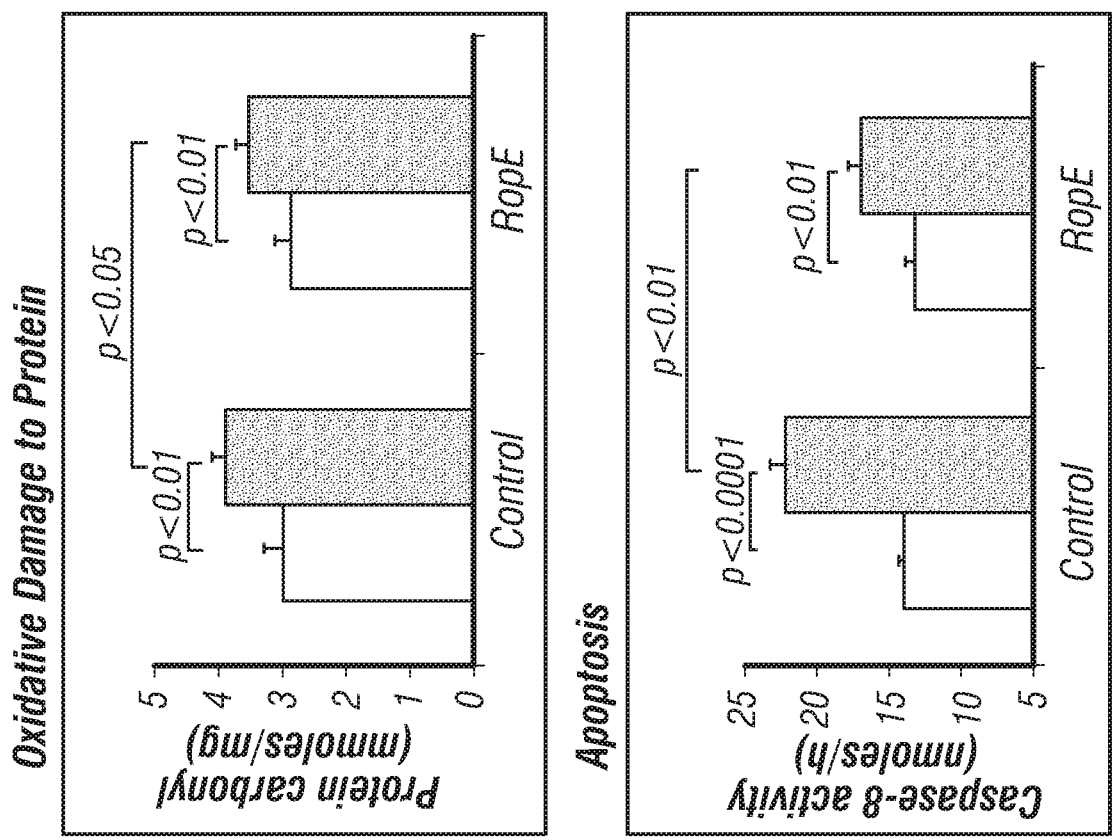
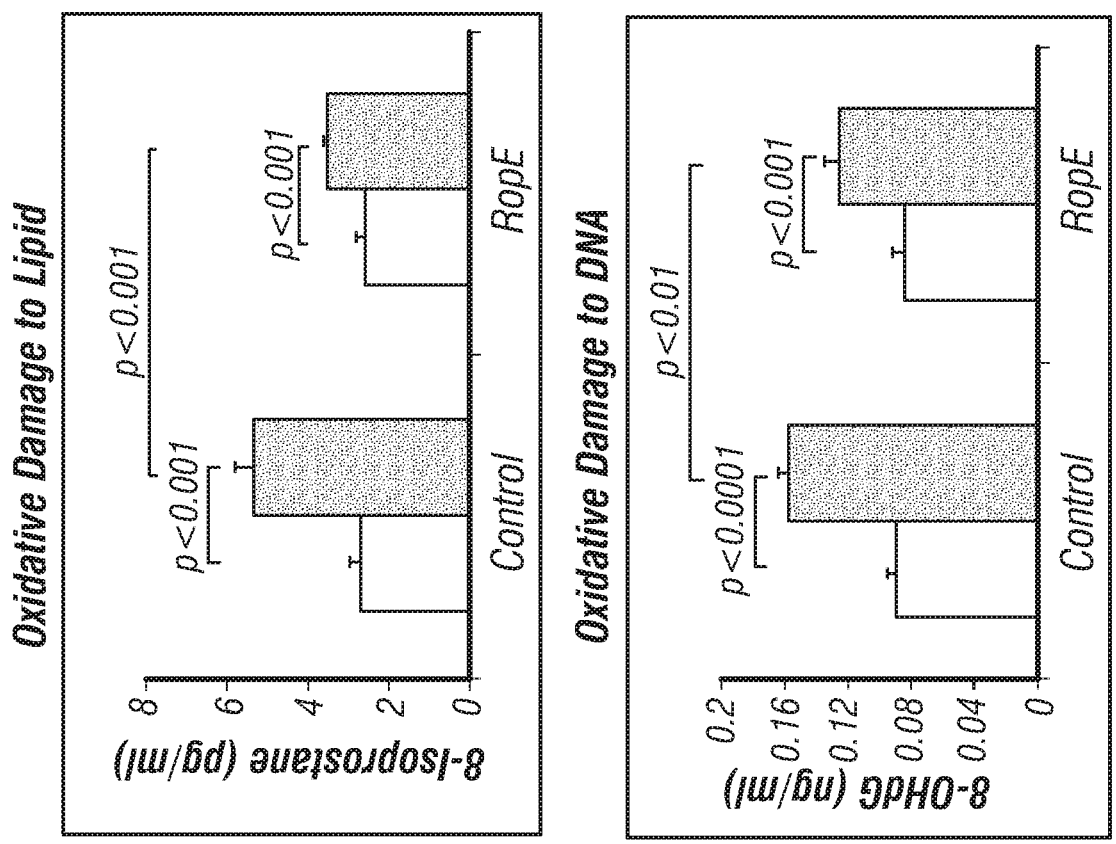
FIG. 4B

Distal lung stained with trichrome. Bar=100μm

```
Hs   ------------------------MPAAGPPLLLLGTPGSALLFAAALEAAGEGQGPVLF
Pt   MAETLRRVLTKGAAWSGEENTPAAGPPLLLLGTPGSGKTALLFAAALEAAGEGQGPVLF
Mm   MAETLRRVLTRDGAAWSGEENTAAAGPPLLLLGAPGSGKTALLFAAALEAAGEGQGPVLF
Cf   MAETLRRVLNQGSSAESGEEYTAEAGPPLLLLGGPGSGKTALLFAAALEAAGEGRGPVLF
Bt   MAETLRRVLNLGIAAGPGK-NTAEAEPPLLLLGPPGSGKTALLFAAALEAAGEGRGPVLF
                              *  ******  .:****************.****

Hs   LTRRPLQSMPRGTGTTLDPMRLQKIRFQYPPSTRELFRLLCSAHEAPGPAPSLLIDGLE
Pt   LTRRPLQSMPRGTGTTLDPMRLQKIRFQYPPSTRELFRLLCSAHEAPGPAPSLLIDGLE
Mm   LTRRPLQSLPRGTGTTLDPMRLQKIRFQYPPSTRELFRLLCSAHEAPGPAPSLLIDGLE
Cf   LTRRPLQSLPRGTGAALDPLRLQKIRFQYPPSTHELQLLCSAHEALGPAPSLLIDGLE
Bt   LTRRPLQSIPRRTGPALEPLRIQKIRFQYPPSTRELFICSAHEARGPAPSLLIDGLE
     ********:**.**. :.* *::**************.**:  *****. ****:****

Hs   EYLAEDPEPQEAAYLIALLLDTAAHFSHRLGPGRDCGLMVALQTQEEA-GSGDVLHLALL
Pt   EYLAEDPEPQEAAYLIALLLDTAAHFSHRLGPGRDCGLMVALQTQEEA-DSGDVLHLALL
Mm   EYLAEDPEPQEAAYLIALLLDTAAHFSHRLGPGRDCGLMVALQTQKEA-DSGDVLHLALL
Cf   EYLVED--SQEAAYLAALLLDTAAHFSHRTGPGQGCGLIVALQTQEEE-ESGDGLQLSLL
Bt   EYLVEDPGSQEAAYLAALLLDTAVHFSHRVGPGRGCGLIVALQTQEEGGDSGNALQLALL
     ***:**    ***** *******.***** ***: *.*:**:**:*    .*: : ::

Hs   QRYFPAQCWLQPDAPGPGEHGLRACLEPGGLGPRTEWWVTFRSDGEMMTAPWPTQAGDPS
Pt   QRYFPAQCWLQPDAPGPGEHGLRACLEPGGLGPRTEWWVTFRSDGEMMTAPWPTQAGDPS
Mm   QRYFPAQCWLQPDAPGPGEHGLRACLDPGGLGPRTEWWVTFRSDGEMMTAPWPTQAGDPS
Cf   QRYFPAQCWLQVDAPGPGQRGLRACLDSGGLSPRAEWWVAFRPDGEMTTPWPTQSGNPN
Bt   QRYFPAQCWLQPDAAGPGQCCLRASLEPGGLGPREEWWVIFQPDGEMTVTRRPTQAVDTS
     *********** **.***:  **: *: ***.**  ***. *: **** .   **. : :

Hs   SGKGSSSGGQP
Pt   SGKGSSSGGQP
Mm   SGKGSSSGGQP
Cf   SDKGSSSGGQP
Bt   SHKGSSSGGQP
     *.*********
```

FIG. 6A

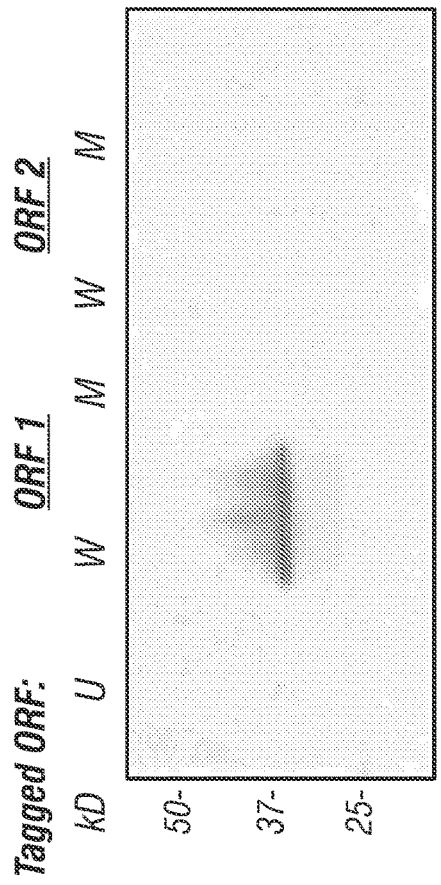

FIG. 6B

Expression of ROPE in E. coli

HHHHHH MPAAGPPLLILGTPGSGKTALLFAAALEAAGEGRGPVLFLTRRPLQSLPRGTGAALDPLRLQKIR
FQYPPSTHELLQLLCSAHEALGPAPSLLLDGLEEYLVEDSQEAAYLAALLDTAAHFSHRTGPG
QGCGLIVALQIQEEESGDGLQLSLLQRYFPAQCWLQVDAPGPGQRGLRACLDSGGLSPRAEWWV
AFRPDGEMTITPWPTQSGNPNSDKGSSSGGQP

Sequence 240 aa
Calculated molecular weight: 26Da
Estimated pI: 5.9

FIG. 7

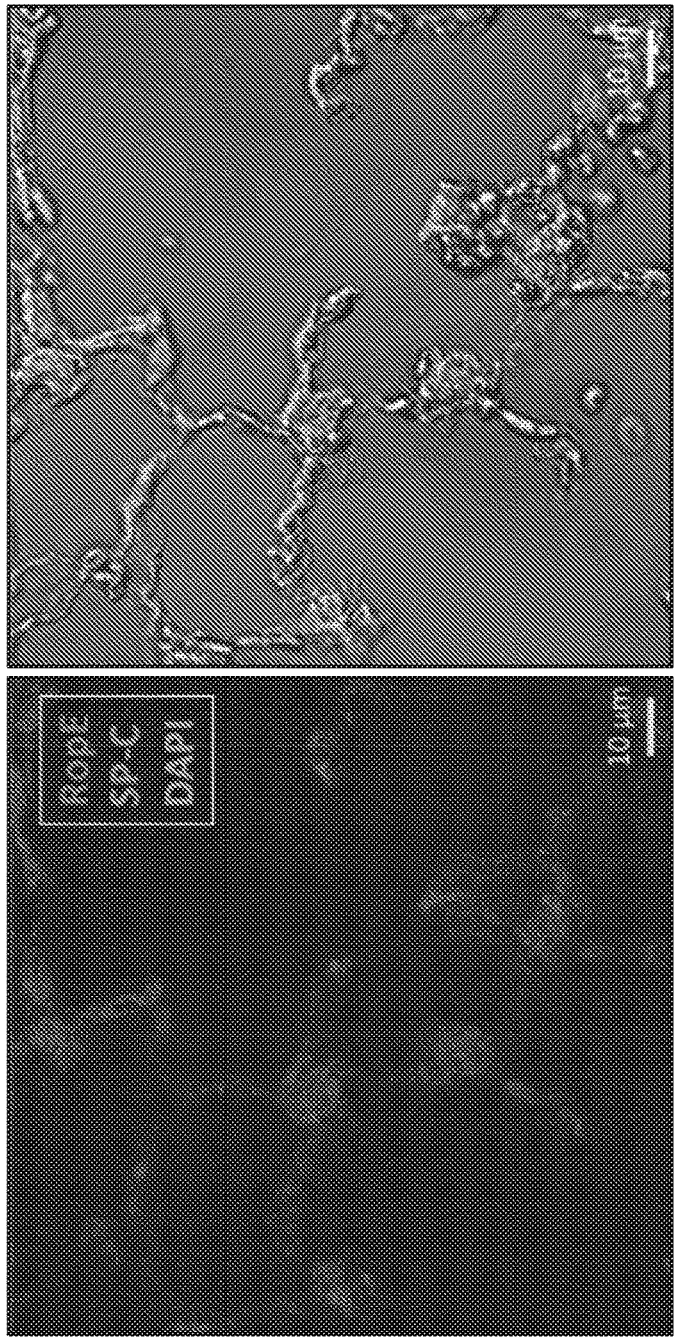
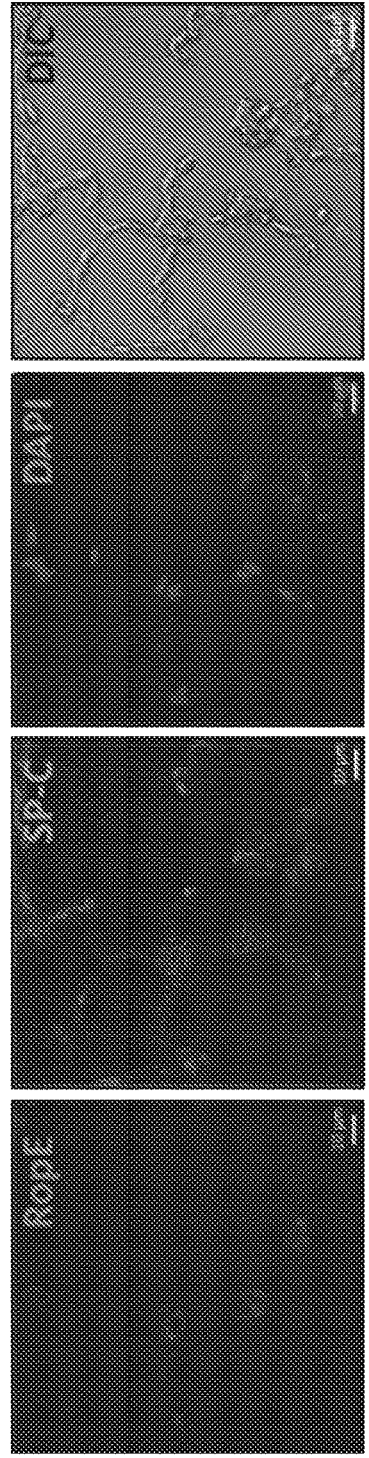
FIG. 11

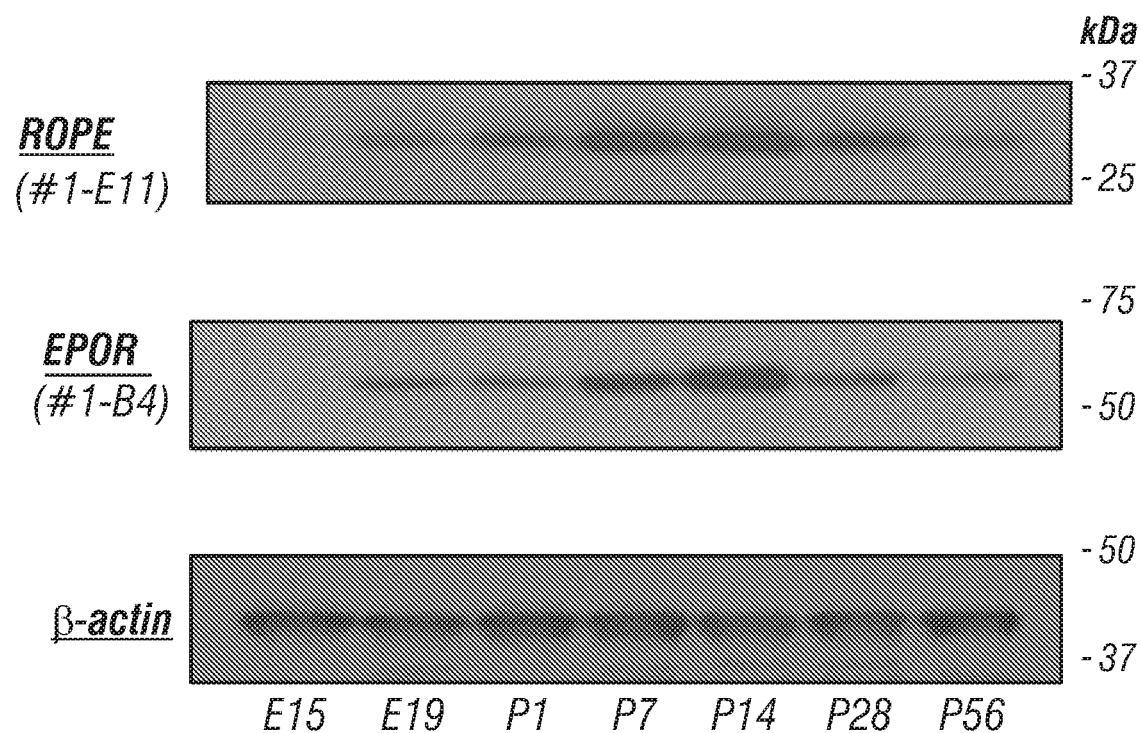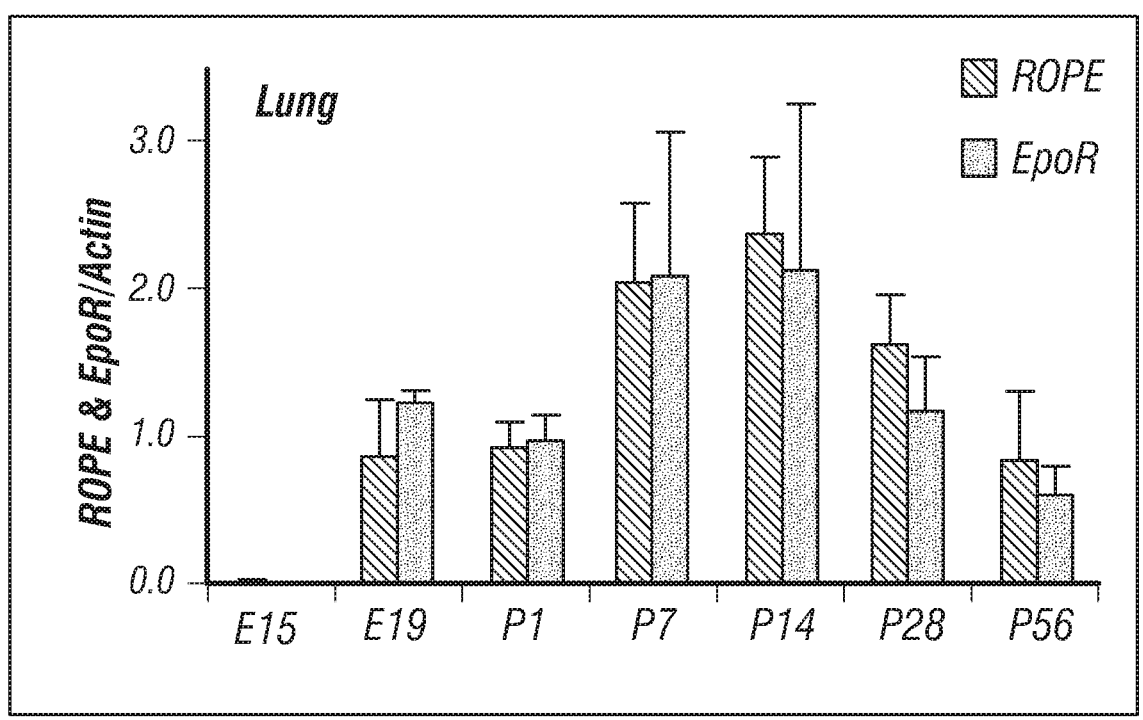
FIG. 12

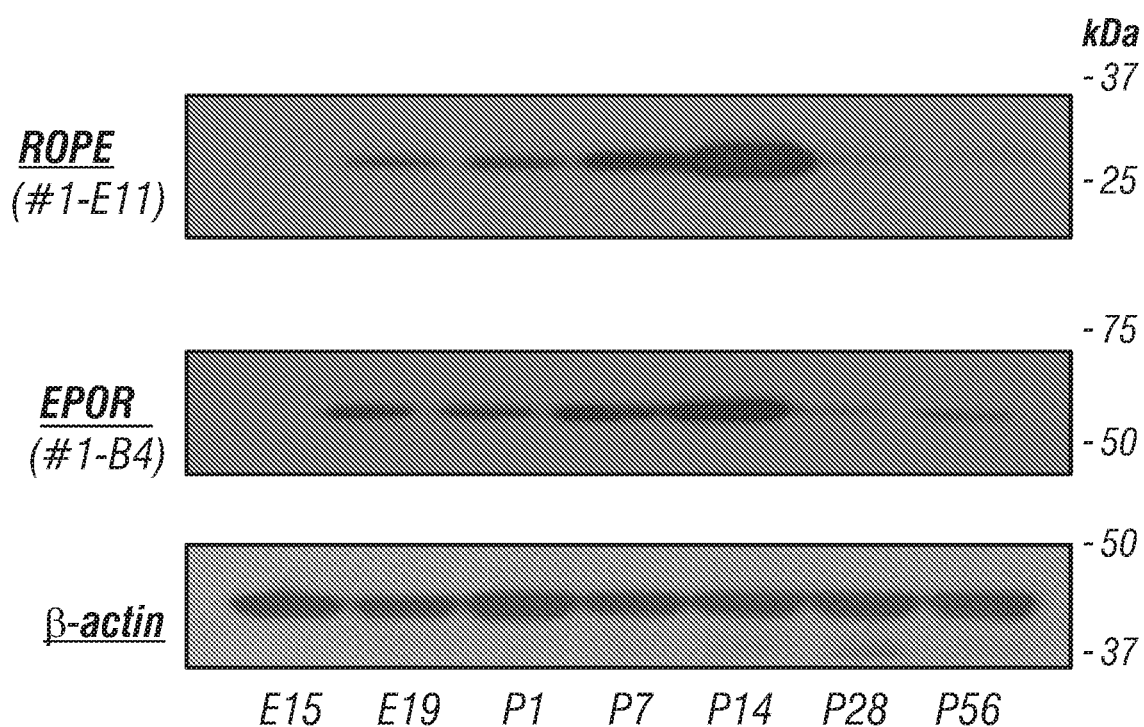
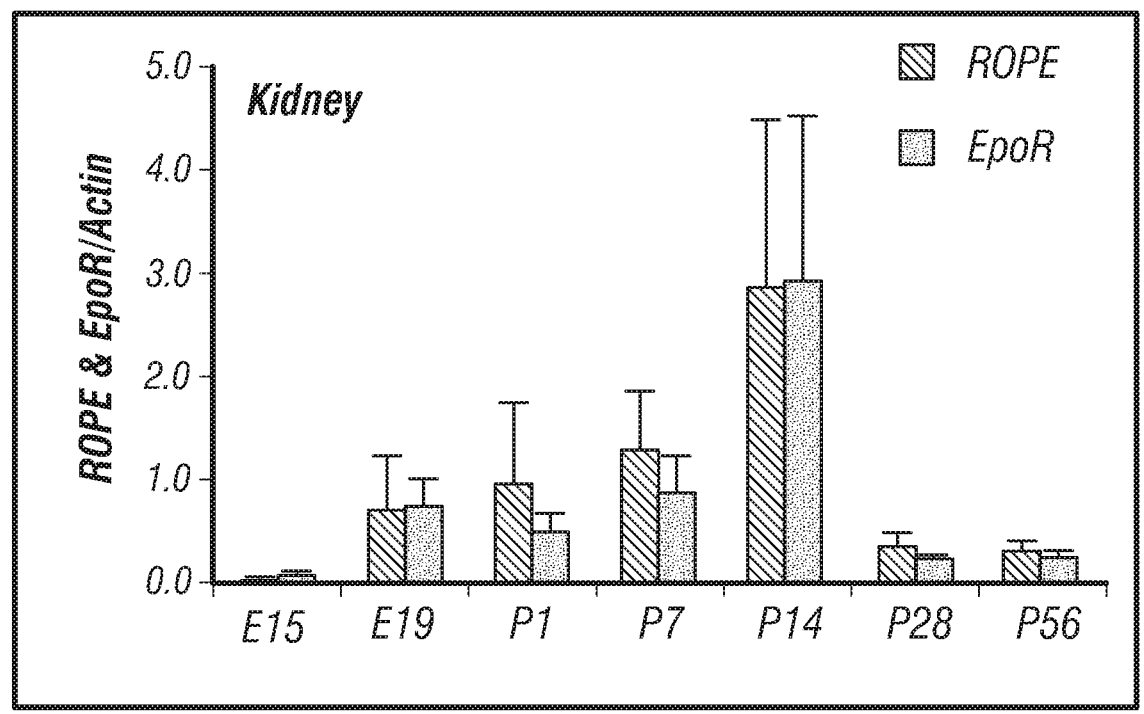
FIG. 12
*(Cont'd)*

COMPOSITIONS COMPRISING ANTISENSE-ENCODED ERYTHROPOIETIN RECEPTOR AND USE THEREOF

This application is a national phase application under 35 U.S.C. § 371 of International Application No. PCT/US2017/050911, filed Sep. 11, 2017, which claims benefit of priority to U.S. Provisional Application Ser. No. 62/394,474, filed Sep. 14, 2016, the entire contents of each of which are hereby incorporated by reference.

This invention was made with government support under grant numbers HL111146 and HL110967 awarded by the National Institutes of Health. The government has certain rights in the invention.

BACKGROUND

1. Field

The present disclosure relates generally to the fields of molecular biology and medicine. More particularly, it concerns antisense-encoded erythropoietin receptor and use thereof in treating and preventing lung disorders.

2. Description of Related Art

Lung diseases including chronic obstructive pulmonary disease, asthma, infections, as well as acute and chronic lung injury leading to fibrosis, constitute the third leading cause of death world-wide (Murray et al., 1997; Rabe et al., 2007; Tsushima et al., 2009). Acute lung injury (ALI) is a serious medical problem amongst American military personnel. ALI during combat can result from very broad etiologies.

First, there can be direct injury via inhalation which can be mediated by physical or thermal trauma, inhalation exposure to particulate matter, toxic or irritant chemicals such as carbon monoxide, cyanide, nitrogen dioxide, or non-explosive aerodynamic dispersion of chemical and biologic warfare agents. Second, even in the absence of direct lung injury, there is a high incidence of secondary ALI, often termed acute respiratory distress syndrome (ARDS) that develops in subjects suffering combat-related trauma to other organs, extensive burns, hemorrhagic shock or sepsis. For example, critically ill patients with acute kidney injury often develop ARDS requiring ventilation. The coexistence of renal failure and ARDS imparts a colossal increase in mortality to more than 80% (Chertow et al., 1995).

ALI from inhalational injury has been treated with inhaled anticoagulants, steroids, beta-agonists, high frequency ventilation, and extra-corporeal membrane oxygenation, with variable and, in general, suboptimal results. No effective preventive measures are available other than barriers with respiratory masks. The management of ARDS has progressed significantly but remains largely supportive with watchful waiting for endogenous healing mechanisms to take effect; and in-hospital mortality remains above 40% (Matthay et al., 2012). Survivors of ALI often suffer chronic respiratory disability with reduced quality of life. Any modalities that can accelerate recovery and/or prevent later complications such as chronic respiratory insufficiency and pulmonary fibrosis will be highly desirable. There is a dire need to improve the early diagnosis and much more importantly, prevention and therapy of combat-related ALI for the men and women in the military. The pathophysiology of ALI from direct inhalational lung injury or ARDS consequent to systemic illness is extremely complex and heterogeneous, encompassing systemic as well as local cardiopulmonary factors such as increased membrane permeability, influx of inflammatory cytokines, oxidative cellular damage, compartmental fluid shifts, deranged ion channels, and many others (Matthay et al., 2012). Clearly, novel treatments are needed for treating and preventing lung disorders such as ALI.

One approach is to first study and then mimic the endogenous cytoprotective and repair response when lungs are damaged, and simulate and amplify those pathways to augment growth and repair. The erythropoietin receptor (EpoR), which mediates the action of erythropoietin to stimulate bone marrow red blood cell production, is also widely expressed in many tissues where its diverse extra-erythropoietic bioactivities include cytoprotection during ischemia, anti-apoptosis, promotion of cell growth, and pro-angiogenesis (Brines and Cerami, 2006) EpoR is abundantly expressed in the lung and is upregulated during developmental and compensatory lung growth (Foster et al., 2004; Zhang et al., 2008). In addition, acute elevation of EpoR expression in the lung by exogenous gene delivery protects the lung from oxidative damage. Thus, strategies to exploit the cytoprotective benefits of the Epo-EpoR axis may provide improved therapeutics for lung disorders.

SUMMARY

Embodiments of the present disclosure provide compositions comprising antisense-encoded erythropoietin receptor (RopE). A first embodiment provides a nanoparticle comprising RopE protein and/or a nucleic acid encoding RopE. In some aspects, the nucleic acid is a messenger RNA (mRNA), a plasmid DNA (pDNA), or a complementary DNA (cDNA). In particular aspects, the nucleic acid is cDNA. In some aspects, the cDNA is under the control of a constitutive promoter or an inducible promoter. In specific aspects, the constitutive promoter is CMV. In certain aspects, the nanoparticle further comprises erythropoietin receptor (EpoR) protein and/or a nucleic acid encoding EpoR.

In some aspects, the nanoparticle is a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube. In certain aspects, the nanoparticle is a poly (lactic-co-glycolic) (PLGA), poly(lactic acid) (PLA), poly (glycolic acid) (PGA), or chitosan nanoparticle. In one particular aspects, the nanoparticle is a PLGA nanoparticle. In other aspects, the nanoparticle is a lipid-polymer hybrid nanoparticle. In particular aspects, the nanoparticle is a lipid-PLGA hybrid nanoparticle.

In certain aspects, the nanoparticle is generated via a double emulsion method. In particular aspects, the double emulsion method is performed using PLGA in chloroform for the primary emulsion and adding polyvinyl alcohol (PVA) for the double emulsion.

In some aspects, the nanoparticle further comprises a cryoprotectant. In particular aspects, the cryoprotectant is glucose.

In certain aspects, the nanoparticle has a diameter between 150 nm to 250 nm, such as between 100 nm to 200 nm. In some aspects, the nanoparticle has a diameter between 175 nm to 225 nm.

In additional aspects, the nanoparticle further comprises an imaging agent. In some aspects, the imaging agent is a chromophore, fluorophore, or radioisotope. In particular aspects, the imaging agent is superparamagnetic iron oxide.

In further aspects, the nanoparticle further comprises a targeting molecule. In particular aspects, the targeting molecule enhances delivery to alveolar type II epithelial cells. In specific aspects, the targeting molecule is an anti-surfactant protein antibody or fragment thereof.

A further embodiment provides a pharmaceutical composition comprising nanoparticles according to the embodiments (e.g, comprising RopE protein and/or nucleic acid) and a pharmaceutically acceptable excipient. In some aspects, the pharmaceutical composition is formulated for inhalation, aerosols, lung delivery, nasal delivery, airway instillation, oral administration, mucosal application, or vascular injection into a vein or artery.

Another embodiment provides e method for treating or preventing a lung disorder in a subject comprising administering a therapeutically effective amount of an antisense-encoded erythropoietin receptor (RopE) protein and/or a nucleic acid encoding RopE to the subject. In some aspects, treating or preventing results in increased lung growth, increased lung repair, reduced tissue edema, increased DNA repair, and/or decreased apoptosis. In some aspects, the method further comprises administering EpoR protein and/or a nucleic acid encoding EpoR. In particular aspects, the subject is a human.

In some aspects, administering is further defined as delivering a nanoparticle according to the embodiments (e.g., comprising RopE protein and/or nucleic acid) discussed above. In certain aspects, the nanoparticles are formulated for inhalational administration.

In certain aspects, the lung disorder is direct or indirect lung injury, acute respiratory distress syndrome, a cancer, an infection, an inflammatory disease, a lung inflammatory disease, asthma, chronic obstructive pulmonary disorder, or an inflammatory disease of the lung parenchyma. In some aspects, the direct or indirect lung injury is an acute lung injury (ALI). In particular aspects, the cancer is lung cancer. In other aspects, the lung disorder is associated with a lung transplant or stem-cell repopulated lungs.

In some aspects, the RopE protein and/or nucleic acid encoding RopE is administered once. In other aspects, the RopE protein and/or nucleic acid encoding RopE is administered two or more times. In certain aspects, one administration leads to sustained expression of RopE for 10 days to 20 days, 20 days to 30 days, 25 days to 35 days, or 40 or more days.

In certain aspects, the method further comprises monitoring uptake of the nanoparticles. In some aspects, monitoring uptake comprises performing magnetic resonance imaging or fluorescent microscopy.

In additional aspects, the method further comprises administering at least one additional therapy. In some aspects, the at least one additional therapy is ventilator support, an anti-inflammatory agent, a chemotherapeutic, or an antibiotic.

Other objects, features and advantages of the present disclosure will become apparent from the following detailed description. It should be understood, however, that the detailed description and the specific examples, while indicating preferred embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) Bidirectional transcription of EpoR gene generates sense (EpoR) and antisense (RopE) transcripts; both are translated into proteins that serve independent yet complementary functions. (FIG. 1B) RopE expression is abundant in normal (left) and malignant human lung tissue (adenocarcinoma and blastoma, middle and right). Fluorescent immunohistochemistry: RopE (red), surfactant protein C (SP-C, green), nuclei (blue). (FIG. 1C) EpoR and RopE expression increase in the remaining canine lung undergoing compensatory lung growth after pneumonectomy (PNX) compared to Sham PNX (n=5). Signals were normalized to 18S rRNA and expressed as a ratio to the mean value in the Sham group. Mean±SEM (FIG. 1D) Lung A549 cells transfected with RopE cDNA are more resistant to hyperoxia-induced damage (lower LDH release) compared to transfection with vector. * $p<0.05$ as well as apoptosis (FIG. 1E).

(FIG. 2A) Purity of His-tagged RopE protein expressed in *E. coli*. (FIG. 2B) Screening of monoclonal antibodies to RopE using HEK-293 cells transfected with FLAG-tagged RopE plasmid. Five clones of anti-RopE monoclonal antibody were obtained. The specificity of the 1-E11 clone was verified by immunoblot (FIG. 2C) and immunocytochemistry (FIG. 2D).

FIGS. 3A-3C: (FIG. 3A) Endogenous RopE transcript is increased during kidney injury (acute kidney injury, AKI, or unilateral nephrectomy, UNX) in rats or during post-pneumonectomy (PNX) compensatory lung growth in canines. Endogenous RopE expression is increased during two types of lung injury in rates including (FIG. 3B) direct lung injury from 90% oxygen for 3 days and (FIG. 3C) indirect lung injury caused by acute ischemia-reperfusion kidney injury.

FIGS. 4A-4D: (FIG. 4A) Immunohistochemistry of RopE expression in fixed lung tissue. Sprague Dawley rats received nebulized RopE cDNA or vector (control) via the trachea followed by 21% or 90% O2 exposure for 3 days. Lung tissue was assayed for RopE expression and biomarkers. Delivery of RopE cDNA successfully increased RopE protein expression in the lung compared to vector-treated controls. Aquaporin-5 (AQP5) serves as a control protein. SYTO stains the nuclei. DIC: differential interference contrast. (FIG. 4B) Lung tissue was assayed for biomarkers of oxidative damage. 8-OHdG: 8-hydroxy-2'-deoxyguanosine. RopE treatment alleviated hyperoxia-induced apoptosis and oxidative damage to protein, DNA, and lipids (B), increased endogenous antioxidant capacity in the lung (FIG. 4C), and ameliorated pulmonary edema and exudation (FIG. 4D). In vector treated control lungs, hyperoxia exposure caused gross lung edema with thickened alveolar septa and exudation into alveolar air spaces. RopE treated lungs showed minimal edema and exudation, clear air spaces and near normal morphology compared to control lungs at baseline (21% $O_2$).

FIGS. 6A-B: (FIG. 6A) Sequence alignment of the putative proteins coded by ORF1 in 5 mammalian species (Hs, Homo sapiens LOC126074; Pt, Pan troglodytes LOC455727; Mm, Macaca mulatta LOC716529; Cf, Canis lupus familiaris LOC611130; Bt, Bos taurus L00507152). Asterisks (*), identical amino acids in all sequences. Colons (:), conserved substitutions. Periods (.), semi-conserved substitutions. The putative ATP/GTP binding P-loop (Walker A) motif is highlighted in black; the putative clathrin binding motif is in gray. Based on European Bioinformatics Institute (EBI) InterPro integrated sequence analysis service for protein families. Top to bottom are SEQ ID NOS: 2-6. (FIG. 6B) Lysates from cells transfected with FLAG-tagged RopE cDNA probed with anti-FLAG on immunoblot.

FIG. 11: Immunohistochemical localization of RopE expression in paraformaldehyde-fixed murine lung tissue using the newly developed MAb. RopE expression is discrete compared to that of EpoR, and co-localized with that of SP-C, a marker of alveolar type-II epithelium. DAPI stains the nuclei. DIC: differential interference contrast.

FIG. 12: To establish the developmental patterns of EpoR and RopE expression, lungs and kidneys were harvested from fetal and postnatal rats at different ages, and probed for EpoR and RopE expression by immunoblot using the new MAbs. Signals were quantified by densitometry and normalized by that of β-actin. There is little expression of EpoR or RopE in the lung (left) or the kidney (right) on embryonic day 15 (E15). In both organs, RopE and EpoR increase with age from embryonic (E19) day to early postnatal life (P7, P14, P28, P56 days), peaking by P7 to P14 days, then declining with age (P28 and P56 days). The window of peak lung expression (P7 to P14 days) coincides with the period of rapid lung cell proliferation and maturation, i.e., transition from the saccular stage to the alveolar stage of lung development that is associated with marked increases in alveolar-capillary surface area and gas exchange efficiency. Mean±SD. Triplicate assays used independent lung samples.

DESCRIPTION OF ILLUSTRATIVE EMBODIMENTS

Figure 1A:
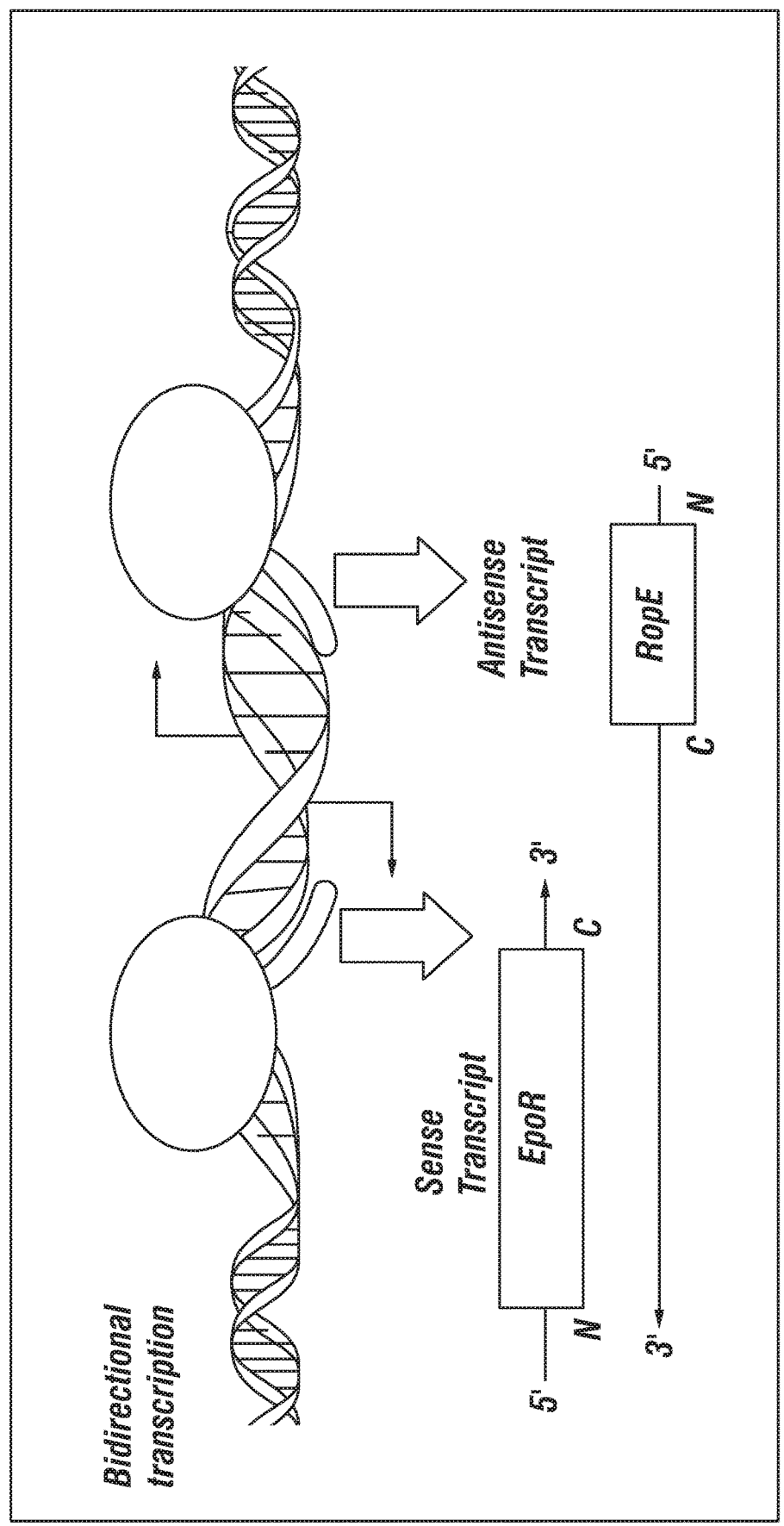
FIGS. 1A-1E.

Erythropoietin (Epo) signaling via its receptor (EpoR) stimulates bone marrow red cell production. In addition, endocrine, paracrine, and autocrine Epo-EpoR signaling is widely present in extra-hematopoietic tissue including the lung, and mediates cytoprotection, anti-apoptosis, angiogenesis, and developmental and compensatory lung growth. The EpoR gene is transcribed in both directions, generating a sense transcript (mRNA) and a naturally occurring non-overlapping antisense transcript (termed RopE). RopE is translated into an antisense protein that forms a part of a protein complex required for in vitro DNA homologous recombination repair (HRR) to ensure genomic stability and prevent malignant transformation of dividing cells. Studies in the present disclosure showed that RopE independently protects lung epithelial cells from acute oxidant injury.

The EpoR-RopE pair is the first example of bi-directional DNA transcription and translation from opposite strands of a single gene yielding both sense and antisense proteins with independent yet complementary functions to coordinately enhance biological objectives, i.e., promoting cytoprotection, growth, and repair while facilitating repair of DNA strand breaks to ensure genomic fidelity.

Accordingly, embodiments of the present disclosure provide compositions comprising RopE alone or in combination with EpoR. RopE and EpoR may be provided as proteins or nucleic acids in a composition for the treatment or prevention of lung disorders including lung cancer and acute lung injury (ALI). In particular aspects, RopE and/or EpoR are provided in nanoparticles, such as PLGA or lipid-PLGA hybrid nanoparticles. The nanoparticles may be formulated for inhalation for delivery to the lungs and can also be targeted to alveolar cells by targeting moieties (e.g., anti-surfactant protein antibody). Thus, the present disclosure provides compositions and methods for the overexpression of either or both proteins of the EpoR-RopE pair via delivery to the lungs in order to prevent the development of and/or enhance recovery from lung disorders such as ALI. These and other aspects of the disclosure are set forth below.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The phrase "effective amount" or "therapeutically effective" means a dosage of a drug or agent sufficient to produce a desired result. The desired result can be subjective or objective improvement in the recipient of the dosage, increased lung growth, increased lung repair, reduced tissue edema, increased DNA repair, decreased apoptosis, a decrease in tumor size, a decrease in the rate of growth of cancer cells, a decrease in metastasis, or any combination of the above.

The term "tumor cell" or "cancer cell" denotes a cell that demonstrates inappropriate, unregulated proliferation. A "human" tumor is comprised of cells that have human chromosomes. Such tumors include those in a human patient, and tumors resulting from the introduction into a non-human host animal of a malignant cell line having human chromosomes.

As used herein the term "targeting molecule" or "targeting moiety" refers to any suitable targeting moiety that can be either chemically conjugated to, or directly complexed with, the nanoparticles provided herein. The term can also refer to a functional group that serves to target or direct a therapeutic agent or anti-cancer agent to a particular location, cell type, diseased tissue, or association. In general, a "targeting ligand" can be directed against a biomarker. The terms "targeting ligand" and "targeting moiety" are used interchangeably throughout.

As used herein, the term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class, including any of the human classes: IgG, IgM, IgA, IgD, and IgE. In exemplary embodiments, antibodies used with the methods and compositions described herein are derivatives of the IgG class. The term antibody also refers to antigen-binding antibody fragments. Examples of such antibody fragments include, but are not limited to, Fab, Fab', F(ab')2, scFv, Fv, dsFv diabody, and Fd fragments. Antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 10 amino acids and more typically will comprise at least about 200 amino acids.

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters.

The term "unit dose" or "dosage" refers to physically discrete units suitable for use in a subject, each unit containing a predetermined quantity of the therapeutic composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

An "anti-cancer" agent is capable of negatively affecting a cancer cell/tumor in a subject, for example, by promoting killing of cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer.

A "chemotherapeutic" drug as used herein refers to those drugs commonly used in the treatment of cancer. These agents act through an apoptotic mechanism of cell death. Each of the drugs can differ in the mechanism by which the cells enter apoptosis.

As used herein, the term "nanoparticle" refers to any particle having dimensions of less than 1000 nanometers (nm). Nanoparticles can be optically or magnetically detectable. In some embodiments, intrinsically fluorescent or luminescent nanoparticles, nanoparticles that comprise fluorescent or luminescent moieties, plasmon resonant nanoparticles, and magnetic nanoparticles are among the detectable nanoparticles that can be used in various embodiments. In general, the nanoparticles should have dimensions small enough to allow their uptake by eukaryotic cells. Typically, the nanoparticles have a longest straight dimension (e.g., diameter) of 200 nm or less. In some embodiments, the nanoparticles have a diameter of 100 nm or less. Smaller nanoparticles, such as having diameters of 50 nm or less, such as about 1 nm to about 30 nm or about 1 nm to about 5 nm, are used in some embodiments. Depending on the shape of the nanoparticle, the size relates to the diameter or length of the respective structure. In various embodiments, the size is the mean particle size.

The term "aerosol" refers to a colloidal system of finely divided solid of liquid particles dispersed in a liquefied or pressurized gas propellant. The typical aerosol of the present disclosure for inhalation may contain a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

"Subject" and "patient" refer to either a human or non-human, such as primates, mammals, and vertebrates. In particular embodiments, the subject is a human.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment.

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in CURRENT PROTOCOLS IN MOLECULAR BIOLOGY (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60, expect=10; Matrix=BLOSUM62; Descriptions=50 sequences; sort by=HIGH SCORE; Databases=non-redundant, GenBank+EMBL+DDBJ+ PDB+GenBank CDS translations+SwissProtein+SPupdate+ PIR.

II. ANTISENSE-ENCODED ERYTHROPOIETIN RECEPTOR (RopE)

Certain embodiments of the present disclosure concern antisense-encoded erythropoietin receptor (termed "RopE") as well as erythropoietin receptor (EpoR). The antisense-encoded erythropoietin receptor is translated into antisense protein ("RopE protein"). In some aspects, the RopE ORF1 protein has the following sequence (SEQ ID NO:1):

MPAAGPPLLLLGTPGSGKTALLFAAALEAAGEGRGPVLFLTRRPLQSLPR

GTGAALDPLRLQKIRFQYPPSTHELLQLLCSAHEALGPAPSLLLLDGLEE

YLVEDSQEAAYLAALLLDTAAHFSHRTGPGQGCGLIVALQIQEEEESGDG

LQLSLLQRYFPAQCWLQVDAPGPGQRGLRACLDSGGLSPRAEWWVAFRPD

GEMTITPWPTQSGNPNSDKGSSSGGQP

Compositions comprising RopE and/or EpoR can include protein and/or nucleic acids encoding RopE or EpoR. In some aspects, the RopE protein provided herein has at least about 80% sequence identity with SEQ ID NO:1, such as at least about 85%, 90%, 95%, or 99% sequence identity with SEQ ID NO: 1.

The RopE protein sequences that can be used in various embodiments include the amino acid sequences described herein, as well as analogues and derivatives thereof. The analogues and derivatives can include, but are not limited to, additions or substitutions of amino acid residues within the amino acid sequences encoded by a nucleotide sequence, but that result in a silent change, thus producing a functionally equivalent gene product. Amino acid substitutions may be made on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Amino acid substitutions may alternatively be made on the basis of the hydropathic index of amino acids. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood in the art (Kyte and Doolittle, *J. Mol. Biol.* 157:105-132, 1982). It is known that in certain instances, certain amino acids may be substituted for other amino acids having a similar hydropathic index or score and still retain a similar biological activity. In making changes based upon the hydropathic index, in certain embodiments the substitution of amino acids whose hydropathic indices are within ±2 is included, while in other embodiments amino acid substitutions that are within ±1 are included, and in yet other embodiments amino acid substitutions within ±0.5 are included.

Amino acid substitutions may alternatively be made on the basis of hydrophilicity, particularly where the biologically functional protein or peptide thereby created is intended for use in immunological embodiments. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments the substitution of amino acids whose hydrophilicity values are within ±2 is included, in certain embodiments those that are within ±1 are included, and in certain embodiments those within ±0.5 are included. One may also identify epitopes from primary amino acid sequences on the basis of hydrophilicity.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

In some embodiments, the RopE and/or EpoR nucleic acid and/or protein are provided in delivery compositions such as liposomes, microcapsules, microparticles, nanoparticles, viral particles, magnetic beads and microdevices, or as fusion protein or conjugates. In particular embodiments, the RopE and/or EpoR are encapsulated in nanoparticles for delivery.

A. Nanoparticle Composition

In some aspects, nanoparticles comprising RopE nucleic acid and/or protein are provided that may be used for inhalation or aerosol delivery. Inhalational drug delivery is a well-established route for targeted delivery of therapeutic agents (small molecules, proteins, and DNA) to the distal lung, and is commonly employed in clinical as well as experimental settings (Azarmi et al., 2008; Ku et al., 2008; Sung et al., 2007). Inhalational delivery takes advantage of the vast alveolar epithelial surface area to allow noninvasive delivery and rapid absorption of a large quantity of drug. Drug particles less than 5 µm in diameter have a high probability of deposition in the lung (Rees et al., 1982) while particles less than 2 µm in diameter tend to concentrate in the alveoli (Zanen et al., 1996; Zanen et al., 1994). Nanoparticles have been used as carrier to deliver therapeutic reagents to the lung. Nanoparticles have the potential to target specific lung cells in the treatment of respiratory disease (Azarmi et al., 2008). Incorporating drugs into nanoparticles provides additional benefits of increased drug concentration and sustained drug release, reducing the overall treatment dose and frequency, thereby decreasing local as well as systemic side effects (Sung et al., 2007).

In some embodiments, the nanoparticles comprise poly (lactic-co-glycolic acid) (PLGA). PLGA nanoparticles (NPs) may be fabricated, e.g., using a modified double emulsion technique as described, e.g., in (Menon et al., 2012). Additional methods that may be used to generate PLGA-containing nanoparticles include those described in, e.g., (Danhier et al., 2012) and (Menon et al., 2014). In some embodiments the nanoparticles are PLGA nanoparticles. In some embodiments, the nanoparticles are surface-modified or bioconjugated, e.g., to improve targeting capability and delivery of an encapsulated drug.

In some embodiments, the nanoparticles may comprise poly(lactic acid) (PLA), poly(glycolic acid) (PGA), and/or PLGA. In some embodiments, the nanoparticle may contain natural polymers such as gelatin and chitosan. In some embodiments, the nanoparticle may contain one or more additional agent such as, e.g., a neutral lipid, a neutral phospholipid, a charged lipid, and/or a charged phospholipid. For example, the neutral phospholipid may be a phosphatidylcholine, such as DOPC, egg phosphatidylcholine ("EPC"), dilauryloylphosphatidylcholine ("DLPC"), dimyristoylphosphatidylcholine ("DMPC"), dipalmitoylphosphatidylcholine ("DPPC"), distearoylphosphatidylcholine ("DSPC"), 1-myristoyl-2-palmitoyl phosphatidylcholine ("MPPC"), 1-palmitoyl-2-myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dimyristyl phosphatidylcholine ("DMPC"), 1,2-distearoyl-sn-glycero-3-phosphocholine ("DAPC"), 1,2-diarachidoyl-sn-glycero-3-phosphocholine ("DBPC"), 1,2-dieicosenoyl-sn-glycero-3-phosphocholine ("DEPC"), palmitoyloeoyl phosphatidylcholine ("POPC"), lysophosphatidylcholine, or dilinoleoylphosphatidylcholine. In certain embodiments the neutral phospholipid is a phosphatidylethanolamine, such as dioleoylphosphatidylethanolamine ("DOPE"), distearoylphophatidylethanolamine ("DSPC"), dimyristoyl phosphatidylethanolamine ("DMPE"), dipalmitoyl phosphatidylethanolamine ("DPPE"), palmitoyloeoyl phosphatidylethanolamine ("POPE"), or lysophosphatidylethanolamine. The charged phospholipid may be positively or negatively charged. The negatively charged phospholipid may be, e.g., a phosphatidylserine (e.g., dimyristoyl phosphatidylserine ("DMPS"), dipalmitoyl phosphatidylserine ("DPPS"), or brain phosphatidylserine ("BPS")) or a phosphatidylglycerol (e.g., dilauryloylphosphatidylglycerol ("DLPG"), dimyristoylphosphatidylglycerol ("DMPG"), dipalmitoylphosphatidylglycerol ("DPPG"), distearoylphosphatidylglycerol ("DSPG"), or dioleoylphosphatidylglycerol ("DOPG")). In some embodiments, the nanoparticles may further comprise chitosan, gelatin, alginate, cholesterol, PEI (polyethyleneimine), and/or polyethyleneglycol (PEG), for example in combination with PLGA. The phospholipid may be a naturally-occurring phospholipid or a synthetic phospholipid. One or more additional surface modification may be included in the nanoparticles, e.g., as described in Enayati et al., 2012; Fields et al., 2012; Ahmed et al., 2012; or Fontana et al., 2001.

The size of the nanoparticles may be varied, as desired. In some embodiments, the nanoparticles are about 10-1000 nm, with a more preferred range of about 50-250 nm in diameter. In some aspects, the present disclosure provides a composition that includes a plurality of particles as described above. In some embodiments, the average characteristic dimension of the plurality of particles is 100 µm or less, e.g., 50 µm or less, 20 µm or less, 10 µm or less, 5 µm or less, 1 µm or less, 500 nm or less, 250 nm or less, or 100 nm or less. In some embodiments, the plurality of particles has a polydispersity index of 0.5 or less, e.g., 0.4 or less, 0.3 or less, 0.2 or less, or 0.1 or less.

In some embodiments, the following method is used to generate PLGA nanoparticles. The emulsion-solvent evaporation method may be used to prepare PLGA nanoparticles. For this procedure, 3% w/v PLGA solution may be prepared in chloroform. The solution may then be added to an aqueous solution of 5% w/v PVA to create an emulsion, and then sonicated. This particle suspension may be stirred (e.g., overnight at room temperature), to allow the solvent to evaporate. Nanoparticles may be recovered by ultracentrifugation at 25,000 rpm for 30 min at 10° C. For drug-loaded nanoparticles, a solution containing the drug (e.g., a therapeutic peptide, protein, small molecule, DNA, cDNA, RNA, RNAi) in water may be emulsified in PLGA solution. If it is desired to include chitosan (or other ingredient) in the nanoparticles, carboxymethyl chitosan (or other ingredient) may be mixed with PVA solution and allowed to be adsorbed onto the surface of the PLGA nanoparticles. If it is desired the nanoparticles may be lyophilized and stored in powder form (e.g., at −20° C.) when not being used. In some embodiments, nanoparticles may be constituted in either DI water, media or saline prior to use.

In some embodiments, the nanoparticles are lipid-polymer hybrid nanoparticles (e.g., described in U.S. Patent Publication No. 2013/0315831; incorporated herein by reference in its entirety). In one aspect, the nanoparticle includes an aqueous core, a first amphiphilic layer surrounding the aqueous core, and a polymeric matrix surrounding the first amphiphilic layer. The particles can further include a second amphiphilic layer surrounding the polymeric matrix. Any or all of the aqueous core, first amphiphilic layer, polymeric matrix, and optional second amphiphilic layer can include one or more active agents (e.g., RopE and/or EpoR nucleic acid and/or protein). Either or both of the first and optional second amphiphilic layer can be a monolayer or a multilayer (e.g., a bilayer). In some embodiments, the first and optional second amphiphilic layers include (independently) naturally derived lipids, surfactants, or synthesized compounds with both hydrophilic and hydrophobic moieties.

In some embodiments, the polymeric matrix includes one or more polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, or polyamines, or combinations thereof. In some embodiments, the polymeric matrix includes a polyalkylene glycol (e.g., polyethylene glycol (PEG)). In some embodiments, the polymeric matrix includes a polyester (e.g., poly(lactide-co-glycolide) (PLGA), polylactic acid, or polycaprolactone). In some embodiments, the polymeric matrix includes copolymer of two or more polymers, such as a copolymer of a polyalkylene glycol (e.g., PEG) and a polyester (e.g., PLGA). In some embodiments, the polymeric matrix includes a lipid-terminated polyalkylene glycol and a polyester. In some embodiments, the polymeric matrix includes lipid-terminated polyethylene glycol (PEG) and poly(lactide-co-glycolide) (PLGA).

In some embodiments, the amphiphilic layer may include, but is not limited to, phospholipids, sphingolipids (e.g., sphingomyelin), diphosphatidylglycerol lipids (e.g., cardiolipin). Exemplary classes of phospholipids include phosphatidic acids, phosphatidylethanolamines, phosphatidylcholines, phosphatidylglycerols, phosphatidylserines, phosphoinositides, phosphatidylinositols, sphingomyelin, lysophosphatidyl derivatives, cardiolipin, and β-acyl-y-alkyl phospholipids. In some embodiments, the amphiphilic compound is a synthetic phospholipid derivative, such as a phosphocholine, phosphoglycerol, phosphatidic acid, phosphoethanolamine, phosphoserine, or PEG phospholipid. Phospholipids and derivatives that may be used can include either saturated or unsaturated lipids, or both. In some embodiments, synthetic phospholipids with asymmetric acyl chains (e.g., with one acyl chain of 6 carbons and another acyl chain of 12 carbons) can also be used. Specific phospholipids that can be used include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), dilignoceroylphatidylcholine (DLPC); phosphatidylethanolamines such as dioleoylphosphatidylethanolamine or 1-hexadecyl-2-palmitoylglycerophosphoethanolamine; phosphocholines such as 1,2-dimyristoleoyl-sn-glycero-3-ethylphosphocholine (EPC14:1); and phosphoethanolamines such as 1,2-distearoyl-sn-glycero-3-phosphoethanolamine (DSPE).

In some embodiments, the nanoparticles are formulated for controlled release. Controlled release occurs when a natural or synthetic polymer and/or amphiphilic compound are combined with one or more active agent in such a way that the active agent(s) are retained within the polymer system for subsequent release in a predetermined manner. Lipid-polymer hybrid particles can release the encapsulated active agents through surface or bulk erosion, diffusion, and/or swelling followed by diffusion, in a time or condition dependent manner. The release of the active agent can be constant over a long or short period, it can be cyclic over a long or short period, or it can be triggered by the environment or other external events (see, e.g., Langer and Tirrell, 2004, *Nature*, 428:487-492). In general, controlled-release polymer systems can provide drug levels in a specific range over a longer period of time than other drug delivery methods, thus increasing the efficacy of the drug and maximizing patient compliance.

In another aspect, the disclosure provides methods of preparing a particle that has an aqueous core, a first amphiphilic layer surrounding the aqueous core, and a polymeric matrix surrounding the first amphiphilic layer. The methods can include the steps of: combining a polymeric material and a first amphiphilic compound in a water immiscible organic solvent to form a water immiscible organic solution; adding an aqueous solution optionally containing a first water miscible solvent to the water immiscible organic solution to form a combination; emulsifying the combination to form a first emulsion solution; and evaporating the water immiscible organic solvent and any water miscible solvent to prepare a particle that has an aqueous core, a first amphiphilic layer surrounding the aqueous core, and a polymeric matrix surrounding the first amphiphilic layer. In some embodiments, the methods further include adding a second aqueous solution containing a stabilizer (e.g., PVA) to the first emulsion solution to form a second combination and emulsifying the second combination to form a second emulsion solution, prior to the step of evaporating the water immiscible organic solvent and any water miscible solvent.

In some embodiments, the nanoparticle further includes one or more additional active agents, e.g., one or more therapeutic, immunomodulatory, or diagnostic agents. Exemplary active agents include biomolecules, bioactive agents, small molecules, drugs, prodrugs, proteins, polypeptides, immunogens, haptens, polynucleotides, and adjuvants. Any or all of the aqueous core, first amphiphilic layer, polymeric matrix, and optional second amphiphilic layer can include one or more active agents.

Exemplary active agents that can be associated with the aqueous core of the particle include biomolecules, bioactive agents, small molecules, drugs, prodrugs, proteins, polypeptides, immunogens, haptens, polynucleotides, and adjuvants. In some embodiments, the active agent associated with the aqueous core can be a polynucleotide, e.g., an expression vector, siRNA, shRNA, microRNA, ribozyme, or antisense polynucleotide. In some embodiments, the polynucleotide includes an immunostimulatory sequence. The active agent associated with the aqueous core can also be a chemotherapeutic drug or prodrug. Exemplary chemotherapeutic drugs and prodrugs include cisplatin, carboplatin, mitaplatin, oxaliplatin, and irinotecan, and derivatives or prodrugs of any thereof. In some embodiments, the active agent associated with the aqueous core is an imaging agent, e.g., a quantum dot, contrast agent, iron oxide nanoparticle, and/or fluorescent moiety. In some embodiments, the active agent associated with the aqueous core is an immunostimulatory agent, e.g., a toll receptor (TLR) ligand ss/dsRNA, polyI:C polynucleotide, or CpG polynucleotide. In some embodiments, the active agent associated with the aqueous core is selected from irinotecan, dexamethasone phosphate, nicardipine hydrochloride, methylsalicylic acid, nitroglycerine, hydrophilic serotonin 5-HT3 receptor antagonists (e.g., ondansetron, granisetron), aminotetralins (e.g., S(−)-2-(N-propyl-N-2-thienylethylamine)-5-hydroxytetralin), and anthracyclines. In some embodiments, the active agent associated with the aqueous core is an inorganic or organometallic compound, e.g., a platinum compound (e.g., carboplatin, mitaplatin, oxaliplatin, or pyriplatin), a ruthenium compound (e.g., trans-[RuCl$_2$(DMSO)$_4$], trans-[RuCl$_2$(imidazole)$_2$]$^-$, trans-[RuCl$_4$(indazole)$_2$]$^-$, etc.), a cobalt compound, a copper compound, or an iron compound. In some embodiments, the active agent associated with the aqueous core is selected from VEGF, fibroblast growth factors, monocyte chemoattractant protein 1 (MCP-1), transforming growth factor alpha (TGF-alpha), transforming growth factor beta (TGF-beta), DEL-I, insulin like growth factors (IGF), placental growth factor (PLGF), hepatocyte growth factor (HGF), prostaglandin E1 (PG-E1), prostaglandin E2 (PG-E2), tumor necrosis factor alpha (TNF-alpha), granulocyte stimulating growth factor (G-CSF), granulocyte macrophage colony-stimulating growth factor (GM-CSF), angiogenin, follistatin, proliferin, PR39, PRI1, nicotine, hydroxy-methylglutaryl coenzyme A (HMG CoA) reductase inhibitors, statins, niacin, bile acid resins, fibrates, antioxidants, extracellular matrix synthesis promoters, inhibitors of plaque inflammation and extracellular degradation, and estradiol. Additional active agents that can be associated with the aqueous core are described herein. Preferably, an active agent associated with the aqueous core is hydrophilic or amphiphilic.

B. Targeting Moiety

In some embodiments, the nanoparticle includes a targeting agent. The target can be associated with a surface of the particle, e.g., covalently bound to the surface of the particle. In some embodiments, the particle includes a second amphiphilic layer and the targeting agent is conjugated to the hydrophilic region of a molecule of the second amphiphilic layer. In exemplary embodiments, the targeting agent includes a nucleic acid aptamer, polypeptide, protein ligand, small molecule, growth factor, hormone, cytokine, interleukin, antibody, antibody fragment, integrin, peptide (e.g., including 50 or fewer, 40 or fewer, 30 or fewer, 25 or fewer, 20 or fewer, 16 or fewer, 12 or fewer, 10 or fewer, 9 or fewer, 8 or fewer, or 7 or fewer amino acids), peptidomimetic, hydrocarbon, small modular immunopharmaceutical, or cell binding sequence. In other exemplary embodiments, the targeting agent includes an affibody, nanobody, adnectin, domain antibody, or an avimer, or any combination thereof.

One specific example of a targeting molecule is specific to alveolar cells, particularly alveolar type II epithelial cells. For example, the targeting molecule may be an anti-surfactant protein (e.g., protein C) antibody or fragment thereof.

The targeting moiety can include any molecule, or complex of molecules, which is/are capable of targeting, interacting with, coupling with, and/or binding to an intracellular, cell surface, or extracellular biomarker of a cell or tissue. The biomarker can include, for example, a cellular protease, a kinase, a protein, a cell surface receptor, a lipid, and/or fatty acid. Other examples of biomarkers that the targeting moieties can target, interact with, couple with, and/or bind to include molecules associated with a particular disease. For example, the biomarkers can include cell surface receptors implicated in cancer development, such as epidermal growth factor receptor and transferrin receptor. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting moieties can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting moiety can include an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)2 fragments), diabodies, tribodies or tetrabodies, which typically are covalently linked or otherwise stabilized (i.e., leucine zipper or helix stabilized) scFv fragments; and receptor molecules, which naturally interact with a desired target molecule.

C. Imaging Agents

In some embodiments, the nanoparticles may be attached to imaging agents of use for imaging and diagnosis of various diseased organs, tissues or cell types, or for monitoring the delivery of the nanoparticles. The protein, nucleic acid or delivery vehicle (e.g., nanoparticle) may be labeled or conjugated with a chromophore, fluorophore or radiotracer for use as an imaging agent. In particular aspects, the imaging agent is superparamagnetic iron oxide. Many appropriate imaging agents are known in the art, as are methods for their attachment to proteins or peptides using metal chelate complexes, radioisotopes, fluorescent markers, or enzymes whose presence can be detected using a colorimetric markers (such as, but not limited to, urease, alkaline phosphatase, (horseradish) hydrogen peroxidase and glucose oxidase).

In some embodiments, the imaging conjugate will also be dual labeled with a radio-isotope in order to combine imaging through nuclear approaches and be made into a unique cyclic structure and optimized for binding affinity and pharmacokinetics. Such agents can be administered by any number of methods known to those of ordinary skill in the art including, but not limited to, oral administration, inhalation, subcutaneous (sub-q), intravenous (I.V.), intraperitoneal (I.P.), intramuscular (I.M.), or intrathecal injection, or as described in greater detail below. In some embodiments the methods and compositions described herein can be used alone or in combination with other techniques, to diagnose, monitor and direct therapy of lung disorders.

1. Chromophore

In some aspects, the imaging agent is a chromophore. Chromophores are molecules capable of selective light absorption resulting in the coloration of these molecule containing compounds. The color arises when a molecule at an excited state releases energy in the form of light with a defined spectrum. Exemplary chromophores include, but are not limited to, a fluorochrome, a non-fluoro chrome chromophore, a quencher (e.g. fluorescence quencher and a dark quencher), an absorption chromophore, a fluorophore, any organic or inorganic dye, metal chelate, or any fluorescent enzyme substrate. In some aspects, the chromophore is a fluorochrome. In some aspects, the fluorochrome is a fluorophore. In some aspects, the chromophore is a quencher. In some aspects, the chromophore is a dark quencher. The compositions provided in the present disclosure may contain different fluorophores and quenchers, such as for FRET assays.

Several chromophores are described in the art, e.g. Beriraan, Handbook of Fluorescence Sprectra of Aromatic Molecules, 2nd Edition, Academic Press, New York, (1971). In examples that utilize fluorescent labels as described herein, any suitable fluorescent label may be used. Exemplary fluorophores suitable for use with the present disclosure includes rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine; cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, pro flavin, acridine orange, acridine yellow, arylmethine derivatives, auramine, crystal violet, malachite green, tetrapyrrole derivatives, porphin, phtalocyanine and bilirubin; 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), Fluorescein dT, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ RholOl, ATTO™ 590, ATTO™ 633, ATTO™ 647N, TYE™ 563, TYE™ 665, and TYE™ 705. In particular aspects, the chromophore is TAMRA.

The detectable label compound may include, but is not limited to fluorodeoxyglucose (FDG); 2'-fluoro-2'deoxy-1beta-D-arabinofuranosyl-5-ethyl-uracil (FEAU); 5-[$^{123}$I]-2'-fluoro-5-iodo-1β-D-arabinofuranosyl-uracil; 5-[$^{124}$I]-2'-fluoro-5-iodo-1β-D-arabinofuranosyl-uracil; 5-[$^{131}$I]-2'-fluoro-5-iodo-1β-D-arabinofuranosyl-uracil, 5-[$^{18}$F]-2'-fluoro-5-fluoro-1-β-D-arabinofuranosyl-uracil; 2-[$^{11}$C]- and 5-([$^{11}$C]-methyl)-2'-fluoro-5-methyl-1-β-D-arabinofuranosyl-uracil; 2-[$^{11}$C]-2'-fluoro-5-ethyl-1-β-D-arabinofuranosyl-uracil; 5-([$^{11}$C]-ethyl)-2'-fluoro-5-ethyl-1-β-D-arabinofuranosyl-uracil; 5-(2-[$^{18}$F]-ethyl)-2'-fluoro-5-(2-fluoroethyl)-1-β-D-arabinofuranosyl-uracil, 5-[$^{123}$I]-2'-fluoro-5-iodovinyl-1-β-D-arabinofuranosyl-uracil; 5-[$^{124}$I]-2'-fluoro-5-iodovinyl-1-β-D-arabinofuranosyl-uracil; 5-[$^{131}$I]-2'-fluoro-5-iodovinyl-1-β-D-arabinofuranosyl-uracil; 5-[$^{123}$I]-2'-fluoro-5-iodo-1-β-D-ribofuranosyl-uracil; 5-[$^{124}$I]-2'-fluoro-5-iodo-1-β-D-ribofuranosyl-uracil; 5-[$^{131}$I]-2'-fluoro-5-iodo-1-β-D-ribofuranosyl-uracil; 5-[$^{123}$I]-2'-fluoro-5-iodovinyl-1-β-D-ribofuranosyl-uracil; 5-[$^{124}$I]-2'-fluoro-5-iodovinyl-1-β-D-ribofuranosyl-uracil; 5-[$^{131}$I]-2'-fluoro-5-iodovinyl-1-β-D-ribofuranosyl-uracil; or 9-4-[$^{18}$F]-fluoro-3-(hydroxymethyl)butyl]guanine.

2. Radionuclide

In some aspects, the imaging agent is a radionuclide. Suitable radionuclide labels are Tc, In, Ga, Cu, F, Lu, Y, Bi, Ac, and other radionuclide isotopes. Particularly, the radionuclide is selected from the group comprising $^{111}$In, $^{99m}$Tc, $^{94m}$Tc, $^{67}$Ga, $^{66}$Ga, $^{68}$Ga, $^{52}$Fe, $^{69}$Er, $^{72}$As, $^{97}$Ru, $^{203}$Pb, $^{62}$Cu, $^{64}$Cu, $^{67}$Cu, $^{186}$Re, $^{188}$Re, $^{86}$Y, $^{90}$Y, $^{51}$Cr, $^{52m}$Mn, $^{157}$Gd, $^{177}$Lu, $^{161}$Tb, $^{169}$Yb, $^{175}$Yb, $^{105}$Rb, $^{166}$Dy, $^{166}$Ho, $^{153}$Sm, $^{149}$Pm, $^{151}$Pm, $^{172}$Tm, $^{121}$Sn, $^{177m}$Sn, $^{213}$Bi, $^{142}$Pr, $^{143}$Pr, $^{198}$Au, $^{199}$Au, $^{18}$F, $^{123}$I, $^{124}$I, $^{131}$I, $^{75}$Br, $^{76}$Br, $^{77}$Br, and $^{82}$Br, amongst others. These radionuclides are cationic and can be complexed with the chelator through the chelating group of the conjugate to form labeled compositions.

In a further aspect a labeled substrate or compound can be labeled with $^{18}$F, $^{277}$Ac, $^{211}$At, $^{128}$Ba, $^{131}$Ba, $^{7}$Be, $^{204}$Bi, $^{205}$Bi, $^{206}$Bi, $^{76}$Br, $^{77}$Br, $^{82}$Br, $^{109}$Cd, $^{47}$Ca, $^{11}$C, $^{13}$C, $^{14}$C, $^{36}$Cl, $^{48}$Cr, $^{51}$Cr, $^{62}$Cu, $^{64}$Cu, $^{67}$Cu, $^{165}$Dy, $^{155}$Eu, $^{153}$Gd, $^{66}$Ga, $^{67}$Ga, $^{68}$Ga, $^{72}$Ga, $^{198}$Au, $^{2}$H, $^{3}$H, $^{166}$Ho, $^{111}$In, $^{113}$In, $^{115}$In, $^{123}$I, $^{125}$I, $^{131}$I, $^{189}$Ir, $^{191}$Ir, $^{192}$Ir, $^{194}$Ir, $^{19}$F, $^{52}$Fe, $^{55}$Fe, $^{59}$Fe, $^{177}$Ln, $^{15}$O, $^{191}$Os, $^{109}$Pd, $^{32}$P, $^{33}$P, $^{42}$K, $^{226}$Ra, $^{186}$Re, $^{188}$Re, $^{82}$Rb, $^{153}$Sm, $^{46}$Sc, $^{47}$Sc, $^{72}$Se, $^{75}$Se, $^{105}$Ag, $^{15}$N, $^{22}$Na, $^{24}$Na, $^{89}$Sr, $^{35}$S, $^{38}$S, $^{177}$Ta, $^{96}$Tc, $^{99m}$Tc, $^{201}$Tl, $^{202}$Tl, $^{113}$Sn, $^{117m}$Sn, $^{121}$Sn, $^{166}$Yb, $^{169}$Yb, $^{175}$Yb, $^{88}$Y, $^{90}$Y, $^{62}$Zn, or $^{65}$Zn. In particular aspects the detectable label is $^{131}$I, $^{125}$I, $^{123}$I, $^{111}$I, $^{99m}$TC, $^{90}$Y, $^{186}$Re, $^{188}$Re, $^{32}$P, $^{153}$Sm, $^{67}$Ga, $^{201}$Tl, $^{77}$Br, or $^{18}$F label.

Two radionuclides commonly used in nuclear imaging and suitable for the present embodiments are the positron emitter $^{18}$F (used in PET), and the gamma ray emitter $^{99m}$Tc (used in SPECT). These radionuclides have relatively short half-lives (109 minutes and 6 hours, respectively) that make them favorable for minimizing exposure of the body to radiation, and have decay characteristics that make them optimal for their respective imaging modalities. However, focusing on PET imaging, the relatively short half-life of $^{18}$F and its typical labeling conditions (use of organic solvents) lowers its suitability for use with biomolecules such as antibodies. An alternative radionuclide may be the positron emitter $^{64}$Cu$^{2+}$.

D. Expression Cassettes

The present disclosure also provides expression constructs including nucleic acids encoding RopE or EpoR In certain embodiments, genetic material may be manipulated to produce expression cassettes and/or expression constructs that encode imaging proteins, and/or therapeutic genes (e.g., RopE and/or EpoR).

A nucleic acid may be made by any technique known to one of ordinary skill in the art, such as for example, chemical synthesis, enzymatic production or biological production. A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

Expression cassettes and/or constructs of the disclosure, whether they encode an imaging protein or a therapeutic gene(s) will typically include various control regions. These control region typically modulate the expression of the gene of interest.

The term promoter will be used here to refer to a group of transcriptional control modules that are clustered around the initiation site for RNA polymerase II. Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. Depending on the promoter, it appears that individual elements can function either cooperatively or independently to activate transcription.

In various embodiments, the human cytomegalovirus immediate early gene promoter (CMVIE), the SV40 early promoter, the Rous sarcoma virus long terminal repeat, β-actin, rat insulin promoter and glyceraldehyde-3-phosphate dehydrogenase can be used to obtain high-level expression of the coding sequence of interest. The use of other viral, retroviral or mammalian cellular or bacterial phage promoters, which are well-known in the art to achieve expression of a coding sequence of interest is contemplated as well, provided that the levels of expression are sufficient for a given purpose. By employing a promoter with well-known properties, the level and pattern of expression of the protein of interest following transfection or transformation can be optimized.

Selection of a promoter that is regulated in response to specific physiologic or synthetic signals can permit inducible expression of the gene product as compared with the cell under non-inducing conditions. Similarly tissue specific or selective promoters may be used to effect transcription in specific tissues or cells so as to reduce potential toxicity or undesirable effects to non-targeted tissues.

III. METHODS OF TREATMENT

In some embodiments, the present disclosure provides methods of treating or preventing lung disorders by administering a therapeutically effective amount of a RopE protein and/or nucleic acid encoding RopE. In some aspects, the RopE protein and/or nucleic acid is administered in combination with EpoR nucleic acid and/or protein. In particular aspects, the RopE and/or EpoR nucleic acid and/or protein are administered as nanoparticles (e.g., PLGA or lipid-PLGA hybrid nanoparticles). In some aspects, the composition is formulated for inhalation, aerosols, lung delivery, nasal delivery, or airway instillation.

The lung disorder can be an acute or chronic lung disorder. In one embodiment, the lung disorder is an acute lung injury, e.g., septic acute lung injury or acute respiratory distress syndrome (ARDS). Lung injury and/or inflammation can be in response to, e.g., exposure to an external agent, e.g., a viral agent (e.g., *Pseudomonas pneumonia*), smoke or asbestos. In other embodiments, the lung disorder can be, e.g., lung or pleural neoplasia, interstitial lung disease and/or organizing pleuitis. In some aspects, the lung disorder is direct or indirect lung injury, acute respiratory distress syndrome, a cancer, an infection, an inflammatory disease, a lung inflammatory disease, asthma, chronic obstructive pulmonary disorder, or an inflammatory disease of the lung parenchyma. In particular aspects, the direct or indirect lung injury is an acute lung injury (ALI). In specific aspects, the cancer is lung cancer. In other aspects, the lung disorder is associated with a lung transplant or stem-cell repopulated lungs. In some aspects, the lung disorder includes bronchospasms, asthma, COPD, chronic bronchitis, emphysema, pulmonary hypertension, asthma, interstitial lung disease, acute respiratory distress syndrome, pneumonia, lung infections, or pulmonary fibrosis that may be induced by inhalable insulin therapy.

The therapeutically effective amount may be administered to the patient in one inhalation or in 2 or more inhalations. In some aspects, the therapeutically effective amount is administered in 2, 3, or 4 inhalations. In some aspects, the method comprises administering the therapeutically effective amount to the patient once a day. In other aspects, the method comprises administering the therapeutically effective amount to the patient two or more times a day.

A. Pharmaceutical Preparations

In some embodiments, the nanoparticles are administered to a mammalian subject (e.g., a human) by inhalation or via an aerosol pharmaceutical composition. Nonetheless, in various embodiments, the pharmaceutical composition may be formulated for parenteral, intravenous, intradermal, intrathecal, intraarterial, intraperitoneal, intranasal, intravaginal, intrarectal, intra-ocular, intramuscular, subcutaneous, mucosal, oral, topical, intra-airway or inhalational administration.

Nanoparticle compositions as described herein, optionally containing a drug or therapeutic agent, may be dissolved or dispersed in a pharmaceutically acceptable carrier. The preparation of an pharmaceutical composition that contains at least one nanoparticle (e.g., containing a drug or therapeutic agent) or additional active ingredient will be known to those of skill in the art in light of the present disclosure, as exemplified by *Remington: The Science and Practice of Pharmacy*, 21$^{st}$ Ed., Lippincott Williams and Wilkins, 2005, incorporated herein by reference. Moreover, for animal (e.g., human) administration, it will be understood that preparations should typically meet sterility, pyrogenicity, general safety and purity standards as required by FDA Office of Biological Standards.

The pharmaceutically acceptable carrier may include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

Nanoparticles described herein may comprise different types of carriers depending on whether it is to be administered in solid, liquid or aerosol form, and whether it need to be sterile for such routes of administration as injection. The present disclosure can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, *Remington: The Science and Practice of Pharmacy*, 21$^{st}$ Ed., Lippincott Williams and Wilkins, 2005).

A drug or active ingredient in a nanoparticle may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

In some embodiments, the nanoparticles or a pharmaceutical composition comprising nanoparticles as described herein may be delivered by intranasal sprays, inhalation, and/or other aerosol delivery vehicles. Methods for delivering compositions directly to the lungs via nasal aerosol sprays has been described, e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The formulations of the embodiments can be aerosolized using any suitable device, including but not limited to a jet nebulizer, an ultrasonic nebulizer, a metered dose inhaler (MDI), and a device for aerosolization of liquids by forced passage through a jet or nozzle (e.g., AERX® drug delivery devices by Aradigm of Hayward, Calif.). For delivery of a formulation to a subject, as described further herein below, an pulmonary delivery device can also include a ventilator, optionally in combination with a mask, mouthpiece, mist inhalation apparatus, and/or a platform that guides users to inhale correctly and automatically deliver the drug at the right time in the breath. Representative aerosolization devices that can be used in accordance with the methods of the present disclosure include but are not limited to those described in U.S. Pat. Nos. 6,357,671; 6,354,516; 6,241,159; 6,044,841; 6,041,776; 6,016,974; 5,823,179; 5,797,389; 5,660,166; 5,355,872; 5,284,133; and 5,277,175 and U.S. Published Patent Application Nos. 20020020412 and 20020020409.

Using a jet nebulizer, compressed gas from a compressor or hospital airline is passed through a narrow constriction known as a jet. This creates an area of low pressure, and liquid medication from a reservoir is drawn up through a feed tube and fragmented into droplets by the air stream. Only the smallest drops leave the nebulizer directly, while the majority impact on baffles and walls and are returned to the reservoir. Consequently, the time required to perform jet nebulization varies according to the volume of the composition to be nebulized, among other factors, and such time can readily be adjusted by one of skill in the art.

A metered dose inhalator (MDI) can be used to deliver a composition of the disclosure in a more concentrated form than typically delivered using a nebulizer. For optimal effect, MDI delivery systems require proper administration technique, which includes coordinated actuation of aerosol delivery with inhalation, a slow inhalation of about 0.5-0.75 liters per second, a deep breath approaching inspiratory capacity inhalation, and at least 4 seconds of breath holding. Pulmonary delivery using a MDI is convenient and suitable when the treatment benefits from a relatively short treatment time and low cost. Optionally, a formulation can be heated to about 25° C. to about 90° C. during nebulization to promote effective droplet formation and subsequent delivery. See e.g., U.S. Pat. No. 5,299,566.

Aerosol compositions of the embodiments comprise droplets of the composition that are a suitable size for efficient delivery within the lung. In some cases, a surfactant formulation is delivered to lung bronchi, more preferably to bronchioles, still more preferably to alveolar ducts, and still more preferably to alveoli. Aerosol droplets are typically less than about 15 μm in diameter, less than about 10 μm in diameter, less than about 5 μm in diameter, or less than about 2 μm in diameter. For efficient delivery to alveolar bronchi of a human subject, an aerosol composition may preferably comprises droplets having a diameter of about 1 μm to about 5 μm.

Droplet size can be assessed using techniques known in the art, for example cascade, impaction, laser diffraction, and optical patternation. See McLean et al. (2000) *Anal Chem* 72:4796-804, Fults et al. (1991) *J Pharm Pharmacol* 43:726-8, and Vecellio None et al. (2001) *J Aerosol Med* 14:107-14.

Protein stability following aerosolization can be assessed using known techniques in the art, including size exclusion chromatography; electrophoretic techniques; spectroscopic techniques such as UV spectroscopy and circular dichroism spectroscopy, and protein activity (measured in vitro or in vivo). To perform in vitro assays of protein stability, an aerosol composition can be collected and then distilled or absorbed onto a filter. To perform in vivo assays, or for pulmonary administration of a composition to a subject, a device for aerosolization is adapted for inhalation by the subject. For example, protein stability can be assessed by determining the level of protein aggregation. Preferably, an aerosol composition of the disclosure is substantially free of protein aggregates. The presence of soluble aggregates can be determined qualitatively using DLS (DynaPro-801TC, ProteinSolutions Inc. of Charlottesville, Va.) and/or by UV spectrophotometry.

In certain aspects, a nebulized composition of the embodiments is produced using a vibrating mesh nebulizer. For example, the composition can be produced with an active vibrating mesh nebulizer (e.g., an Aeroneb® Professional Nebulizer System). Descriptions of such systems and there operation can be found, for instance, in U.S. Pat. Nos. 6,921,020; 6,926,208; 6,968,840; 6,978,941; 7,040,549; 7,083,112; 7,104,463; and 7,360,536, each of which is incorporated herein by reference in its entirety. In yet further aspects, a composition of the embodiments can be produced with a passive vibrating mesh nebulizer, such as the Omron MicroAir® or the EZ Breathe Atomizer.

B. Combination Therapies

In some embodiments, the RopE and/or EpoR compositions provided herein may be administered in combination with at least one additional therapeutic. In some aspects, the at least one additional therapy is ventilator support, an anti-inflammatory agent, a chemotherapeutic, or an antibiotic. In some embodiments, the drug may be an anti-inflammatory drug, a chemotherapeutic, a tissue protective or a growth promoting substance. For example, in some embodiments the drug may be a therapeutic to treat asthma, chronic obstructive pulmonary disorder (COPD), cancer (e.g., a lung cancer), acute lung injury (ALI), or chronic lung fibrosis.

The additional therapy may be a cancer therapy such as radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional cancer therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent. The additional therapy may be one or more of the chemotherapeutic agents known in the art.

Various combinations may be employed. For the example below a RopE and/or EpoR nucleic acid and/or protein is "A" and an additional therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

1. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein tansferase inhibitors, transplatinum, and pharmaceutically acceptable salts, acids, or derivatives of any of the above.

2. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

3. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells Antibody-drug conjugates have emerged as a breakthrough approach to the development of cancer therapeutics. Cancer is one of the leading causes of deaths in the world. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCE-TRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment. As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

In some embodiments, the immunotherapy may be an immune checkpoint inhibitor. Immune checkpoints are molecules in the immune system that either turn up a signal (e.g., co-stimulatory molecules) or turn down a signal. Inhibitory checkpoint molecules that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

The immune checkpoint inhibitors may be drugs such as small molecules, recombinant forms of ligand or receptors, or, in particular, are antibodies, such as human antibodies (e.g., International Patent Publication WO2015016718; incorporated herein by reference). Known inhibitors of the immune checkpoint proteins or analogs thereof may be used, in particular chimerized, humanized or human forms of antibodies may be used. As the skilled person will know, alternative and/or equivalent names may be in use for certain antibodies mentioned in the present disclosure. Such alternative and/or equivalent names are interchangeable in the context of the present disclosure. For example it is known that lambrolizumab is also known under the alternative and equivalent names MK-3475 and pembrolizumab.

In some embodiments, the PD-1 binding antagonist is a molecule that inhibits the binding of PD-1 to its ligand binding partners. In a specific aspect, the PD-1 ligand binding partners are PDL1 and/or PDL2. In another embodiment, a PDL1 binding antagonist is a molecule that inhibits the binding of PDL1 to its binding partners. In a specific aspect, PDL1 binding partners are PD-1 and/or B7-1. In another embodiment, the PDL2 binding antagonist is a molecule that inhibits the binding of PDL2 to its binding partners. In a specific aspect, a PDL2 binding partner is PD-1. The antagonist may be an antibody, an antigen binding fragment thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 axis antagonists for use in the methods provided herein are known in the art such as described in U.S. Patent Application No. 20140294898, 2014022021, and 20110008369, all incorporated herein by reference.

In some embodiments, the PD-1 binding antagonist is an anti-PD-1 antibody (e.g., a human antibody, a humanized antibody, or a chimeric antibody). In some embodiments, the anti-PD-1 antibody is selected from the group consisting of nivolumab, pembrolizumab, and CT-011. In some embodiments, the PD-1 binding antagonist is an immunoadhesin (e.g., an immunoadhesin comprising an extracellular or PD-1 binding portion of PDL1 or PDL2 fused to a constant region (e.g., an Fc region of an immunoglobulin sequence). In some embodiments, the PD-1 binding antagonist is AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PDL2-Fc fusion soluble receptor described in WO2010/027827 and WO2011/066342.

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to CD80 or CD86 on the surface of antigen-presenting cells. CTLA4 is a member of the immunoglobulin superfamily that is expressed on the surface of Helper T cells and transmits an inhibitory signal to T cells. CTLA4 is similar to the T-cell co-stimulatory protein, CD28, and both molecules bind to CD80 and CD86, also called B7-1 and B7-2 respectively, on antigen-presenting cells. CTLA4 transmits an inhibitory signal to T cells, whereas CD28 transmits a stimulatory signal. Intracellular CTLA4 is also found in regulatory T cells and may be important to their function. T cell activation through the T cell receptor and CD28 leads to increased expression of CTLA-4, an inhibitory receptor for B7 molecules.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; Camacho et al., 2004; Mokyr et al., 1998 can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001014424, WO2000037504, and U.S. Pat. No. 8,017,114; all incorporated herein by reference.

An exemplary anti-CTLA-4 antibody is ipilimumab (also known as 10D1, MDX-010, MDX-101, and Yervoy®) or antigen binding fragments and variants thereof. In other embodiments, the antibody comprises the heavy and light chain CDRs or VRs of ipilimumab. Accordingly, in one embodiment, the antibody comprises the CDR1, CDR2, and CDR3 domains of the VH region of ipilimumab, and the CDR1, CDR2 and CDR3 domains of the VL region of ipilimumab. In another embodiment, the antibody competes for binding with and/or binds to the same epitope on CTLA-4 as the above-mentioned antibodies. In another embodiment, the antibody has at least about 90% variable region amino acid sequence identity with the above-mentioned antibodies (e.g., at least about 90%, 95%, or 99% variable region identity with ipilimumab).

Other molecules for modulating CTLA-4 include CTLA-4 ligands and receptors such as described in U.S. Pat. Nos. 5,844,905, 5,885,796 and International Patent Application Nos. WO1995001994 and WO1998042752; all incorporated herein by reference, and immunoadhesions such as described in U.S. Pat. No. 8,329,867, incorporated herein by reference.

4. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

5. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

6. Lung Disorder Therapies

The additional therapy may be any therapeutic used to treat a lung disorder. These can include, but are not limited to, ventilator support, an anti-inflammatory agent, an antibiotic, surgery, steroid therapy, non-steroid therapy, antiviral therapy, antifungal therapy, antimicrobial therapy, immunosuppressant therapy, anti-infective therapy, anti-hypertensive therapy, and nutritional supplements. For example, the pharmaceutical compositions of the present disclosure may further comprise one or more therapeutic agents selected from other bronchodilators (e.g., $PDE_3$ inhibitors, adenosine 2b modulators and $\beta_2$ adrenergic receptor agonists); anti-inflammatory agents (e.g. steroidal anti-inflammatory agents, such as corticosteroids; non-steroidal anti-inflammatory agents (NSAIDs), and $PDE_4$ inhibitors); other muscarinic receptor antagonists (i.e., antichlolinergic agents); anti-infective agents (e.g. Gram positive and Gram negative antibiotics or antivirals); antihistamines; protease inhibitors; and afferent blockers (e.g., $D_2$ agonists and neurokinin modulators).

Representative $\beta_2$ adrenergic receptor agonists that can be used in combination with, and in addition to, the compounds of the present disclosure include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used in combination with the compounds of the present disclosure include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(-3-{[7-({(2R)-2-hydroxy-2-[4-hydroxy-3-(hydroxymethyl)phenyl]ethyl}-amino)heptyl]oxy}-propyl) benzenesulfonamide and related compounds disclosed in WO 02/066422; 3-[3-(4-{[6-([(2R)-2-hydroxy-2-[4-hydroxy-3-(hydroxymethyl)phenyl]ethyl}amino)hexyl] oxy}butyl)-phenyl]imidazolidine-2,4-dione and related compounds disclosed in WO 02/070490; 3-(4-{[6-({(2R)-2-[3-(formylamino)-4-hydroxyphenyl]-2-hydroxyethyl}amino)hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino) hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]-oxy}butyl) benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino)hexyl]-oxy}butyl) benzenesulfonamide and related compounds disclosed in WO 02/076933; 4-{(1R)-2-[(6-{2-[(2,6-dichlorobenzyl) oxy]ethoxy}hexyl)amino]-1-hydroxyethyl}-2-(hydroxymethyl)phenol and related compounds disclosed in WO 03/024439; and pharmaceutically acceptable salts thereof. When employed, the $\beta_2$-adrenoreceptor agonist will be present in the pharmaceutical composition in a therapeutically effective amount. Typically, the β₂-adrenoreceptor agonist will be present in an amount sufficient to provide from about 0.05 μg to about 500 μg per dose.

Representative steroidal anti-inflammatory agents that can be used in combination with the compounds of the present disclosure include, but are not limited to, methyl prednisolone, prednisolone, dexamethasone, fluticasone propionate, 6,9-difluoro-17-[(2-furanylcarbonyl)oxy]-11-hydroxy-16-methyl-3-oxoandrosta-1,4-diene-17-carbothioic acid S-fluoromethyl ester, 6,9-difluoro-11-hydroxy-16-methyl-3-oxo-17-propionyloxy-androsta-1,4-diene-17-carbothioic acid S-(2-oxo-tetrahydrofuran-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the pharmaceutical composition in a therapeutically effective amount. Typically, the steroidal anti-inflammatory agent will be present in an amount sufficient to provide from about 0.05 μg to about 500 μg per dose.

Representative muscarinic antagonists (i.e., anticholinergic agents) that can be used in combination with, and in addition to, the compounds of the present disclosure include, but are not limited to, atropine, atropine sulfate, atropine oxide, methylatropine nitrate, homatropine hydrobromide, hyoscyamine (d, l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., H₁-receptor antagonists) that can be used in combination with the compounds of the present disclosure include, but are not limited to, ethanolamines, such as carbinoxamine maleate, clemastine fumarate, diphenylhydramine hydrochloride and dimenhydrinate; ethylenediamines, such as pyrilamine amleate, tripelennamine hydrochloride and tripelennamine citrate; alkylamines, such as chlorpheniramine and acrivastine; piperazines, such as hydroxyzine hydrochloride, hydroxyzine pamoate, cyclizine hydrochloride, cyclizine lactate, meclizine hydrochloride and cetirizine hydrochloride; piperidines, such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

For example, representative phosphodiesterase-4 (PDE4) inhibitors or mixed PDE3/PDE4 inhibitors that can be used in combination with the compounds of the present disclosure include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one; cis-[4-cyano-4-(3-cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds disclosed in WO99/16766 (Kyowa Hakko); K-34 (Kyowa Hakko); V-11294A (Napp); roflumilast (Byk-Gulden); pthalazinone compounds disclosed in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

IV. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Evaluation of Sense (EpoR) and Antisense (RopE) Strands of Erythropoietin Receptor Gene Balanced transcription and translation from both sense and antisense strands of the EpoR gene is crucial for normal lung cell growth and repair without genomic errors. Imbalance of the sense-antisense EpoR gene expression promotes DNA replication error accumulation, lung cancer development, and progression. Thus, it was hypothesized that restoring sense-antisense EpoR transcript balance would preserve genomic fidelity and retard lung cancer progression.

There is normally bi-directional transcription of the EpoR gene, generating an endogenous non-overlapping antisense EpoR (termed RopE) transcript (FIG. 1A), which is translated into antisense RopE protein. Abundant RopE has been localized in normal and malignant human lung cells and tissue (FIG. 1B). During maturation, RopE transcripts and protein are increased concurrently with EpoR mRNA and protein. RopE expression is further increased by far more than EpoR in post-pneumonectomy (PNX) compensatory lung growth (FIG. 1C). RopE expression protects lung cells against hyperoxic injury (FIG. 1D) with equal potency as EpoR.

Figure 2A:
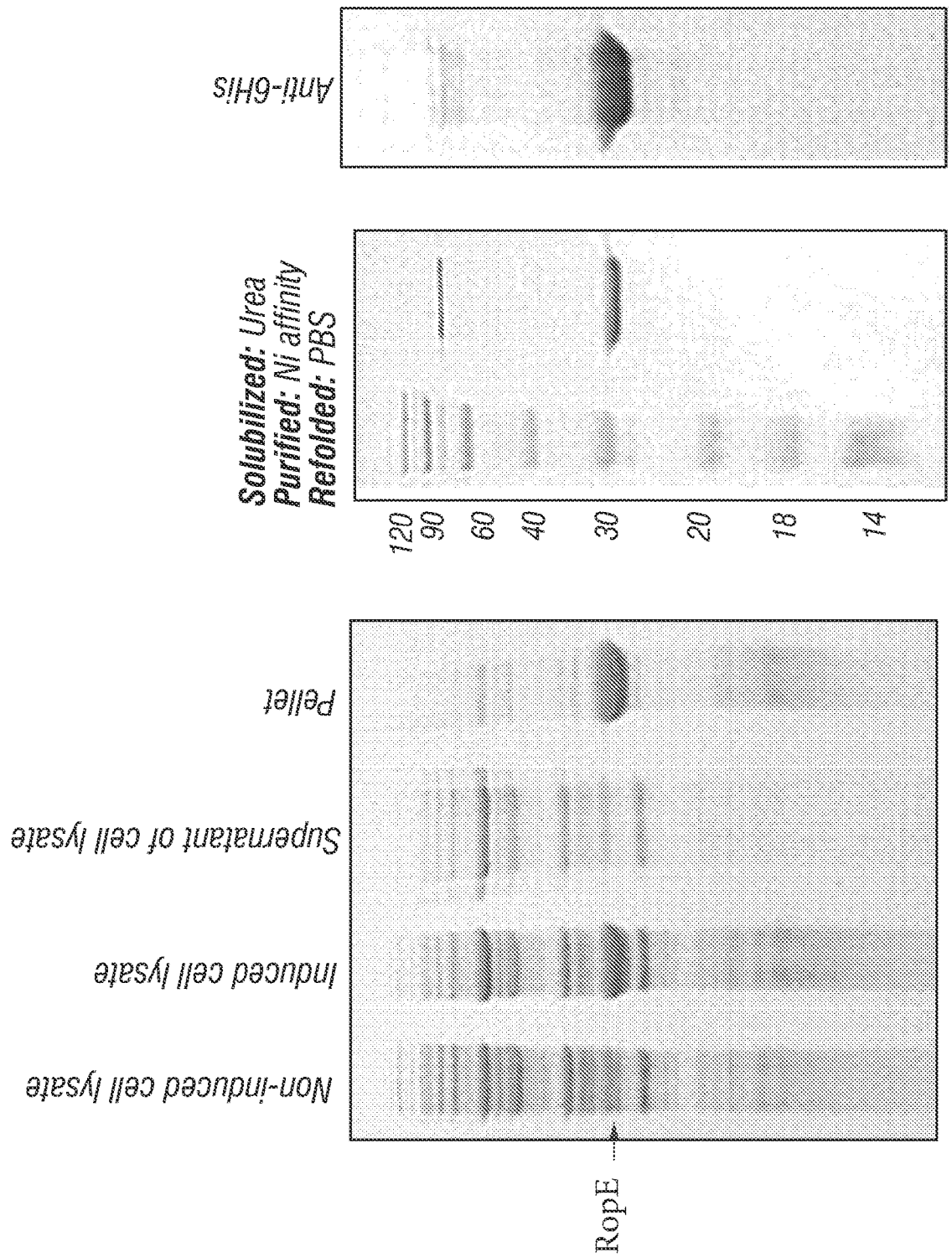
FIGS. 2A-2D.
Figure 2B:
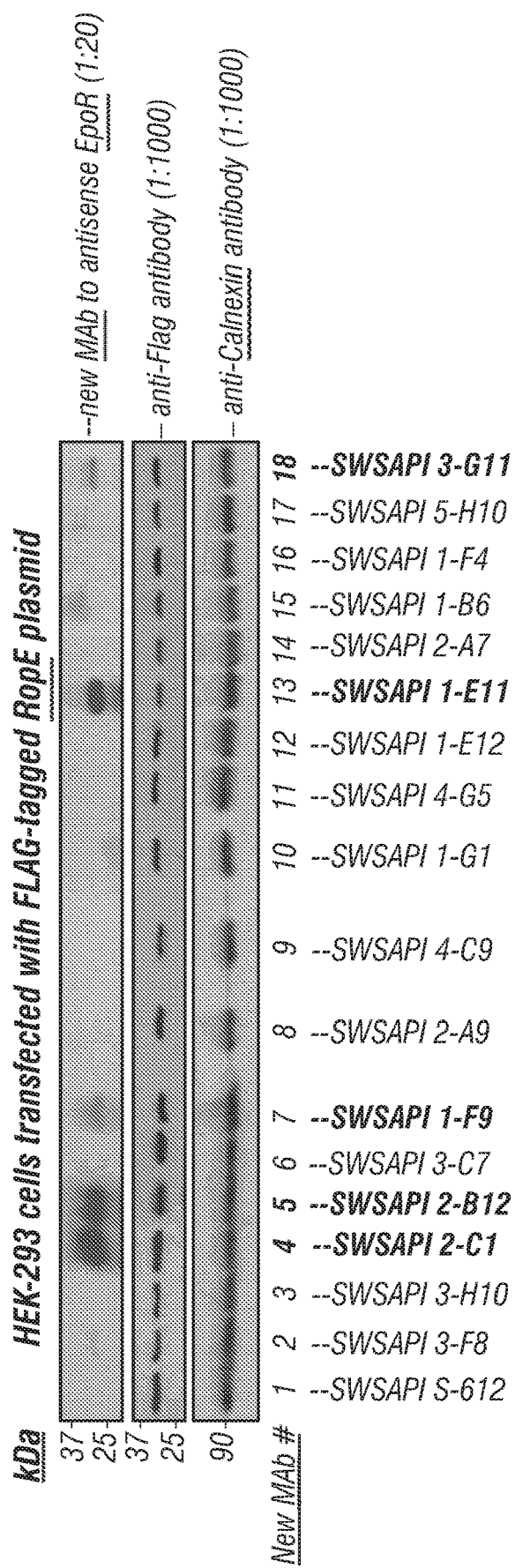
Figure 2C:
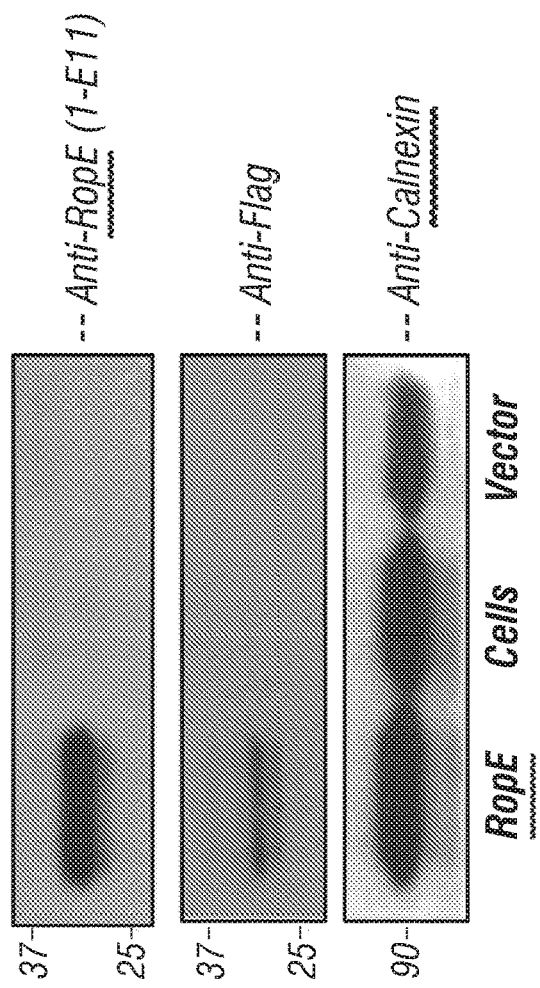
Figure 2D:
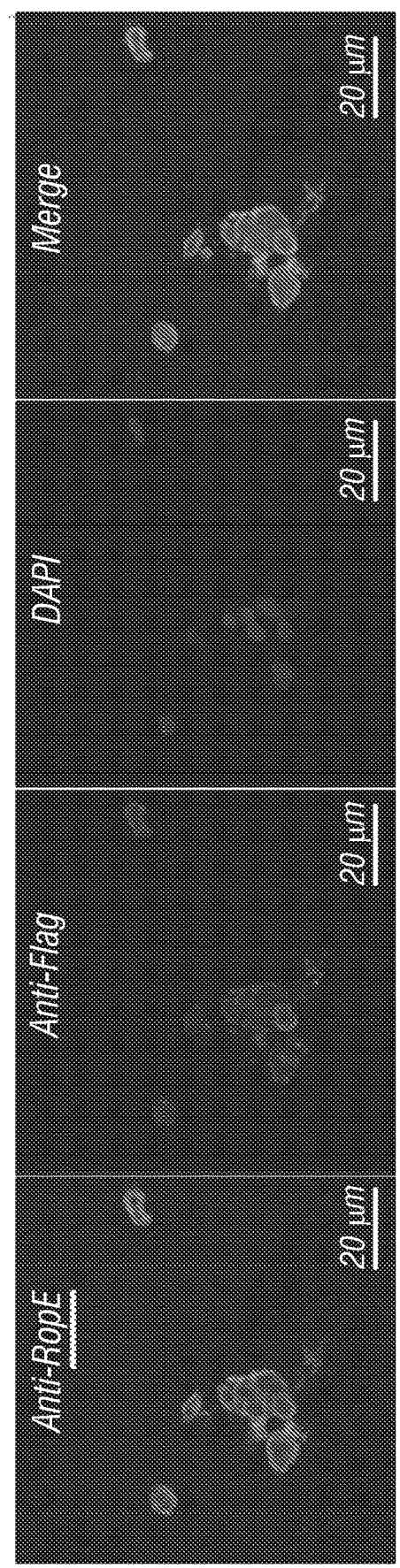

For RopE studies, an anti-RopE monoclonal antibody was developed. A tag of 6 histidines was added N-terminally to the RopE sequence (SEQ ID NO:1) under the control of an inducible IPTG promoter and transformed in E. coli. Protein expression was induced and the cells were pelleted and solubilized in urea (FIG. 2A). The protein was purified using a Nickel affinity column and dialyzed in PBC to remove urea and allow protein refolding. The purified RopE protein was then used for the production of monoclonal antibodies which were screened in HEK-293 cells transfected with FLAG-tagged RopE plasmid (FIG. 2B). Five clones of anti-RopE monoclonal antibody were obtained. The specificity of the 1-E11 clone was verified by immunoblot (FIG. 2C) and immunocytochemistry (FIG. 2D).

Figure 3A:
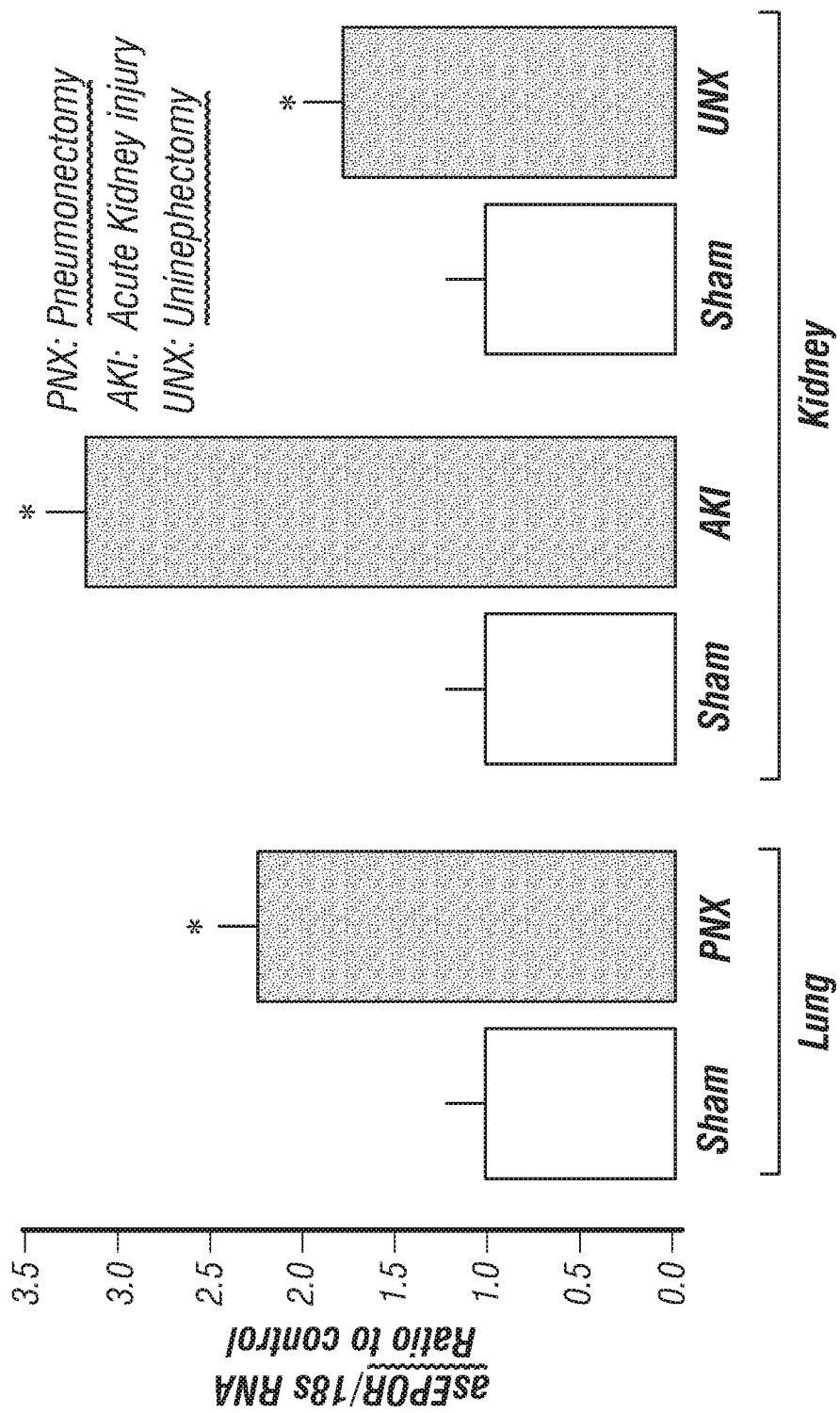
Figure 4A:
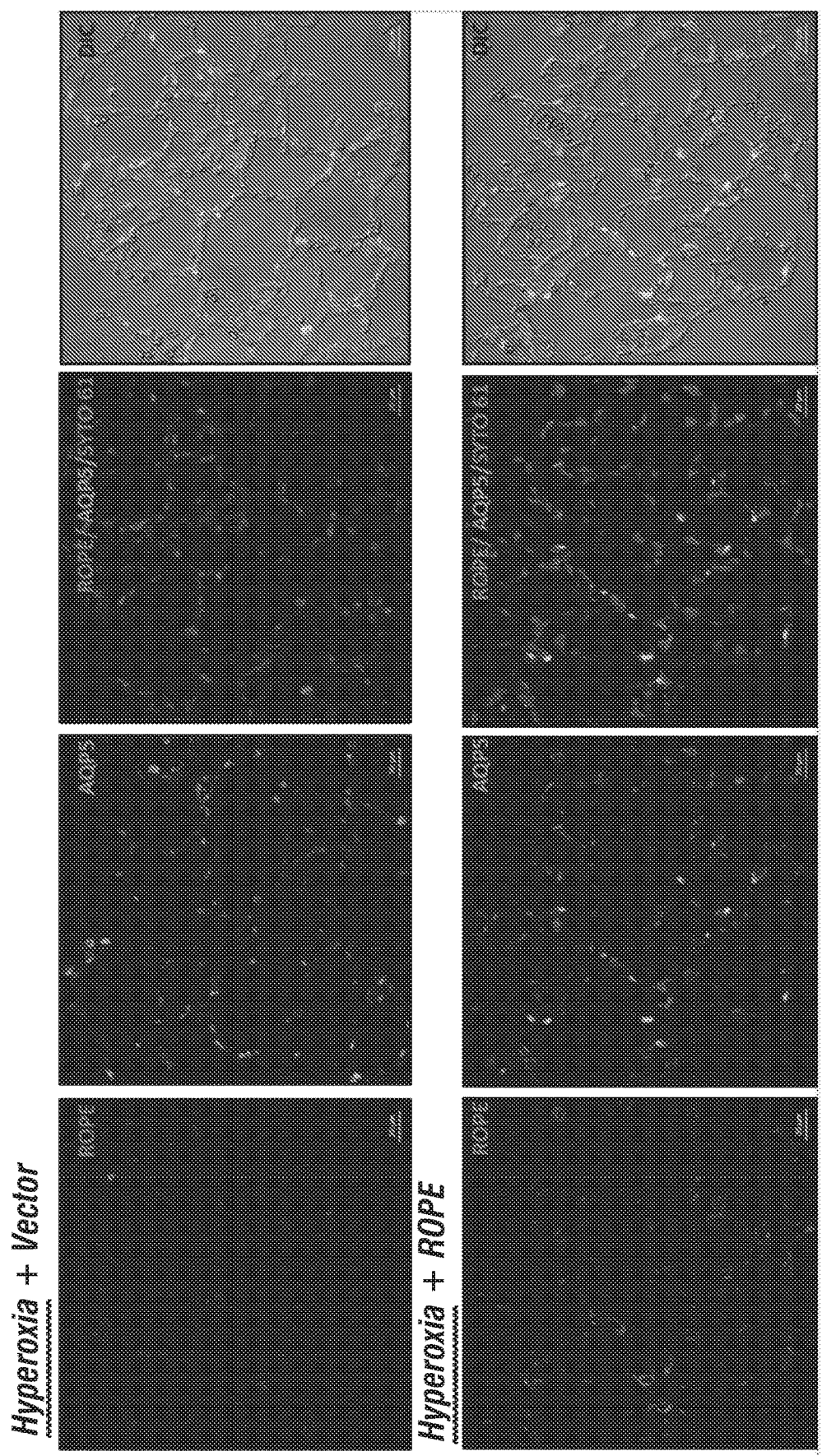
Figure 4C:
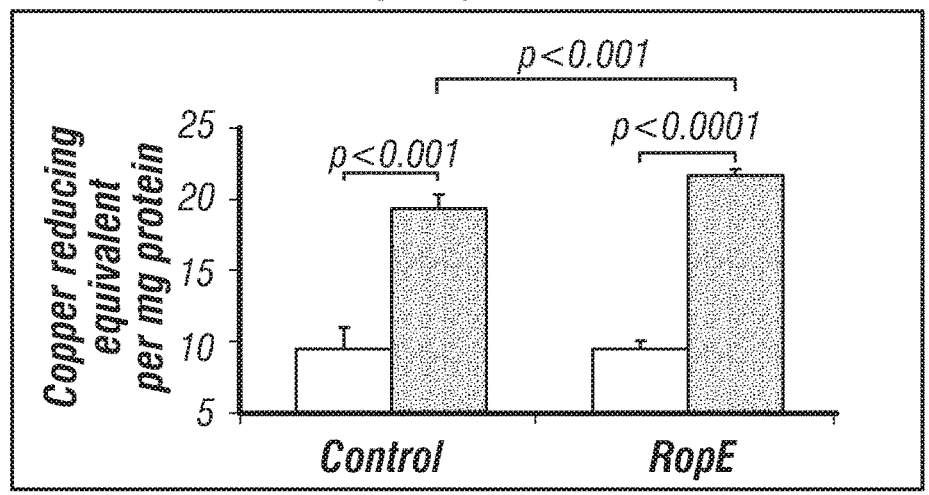
Figure 4D:
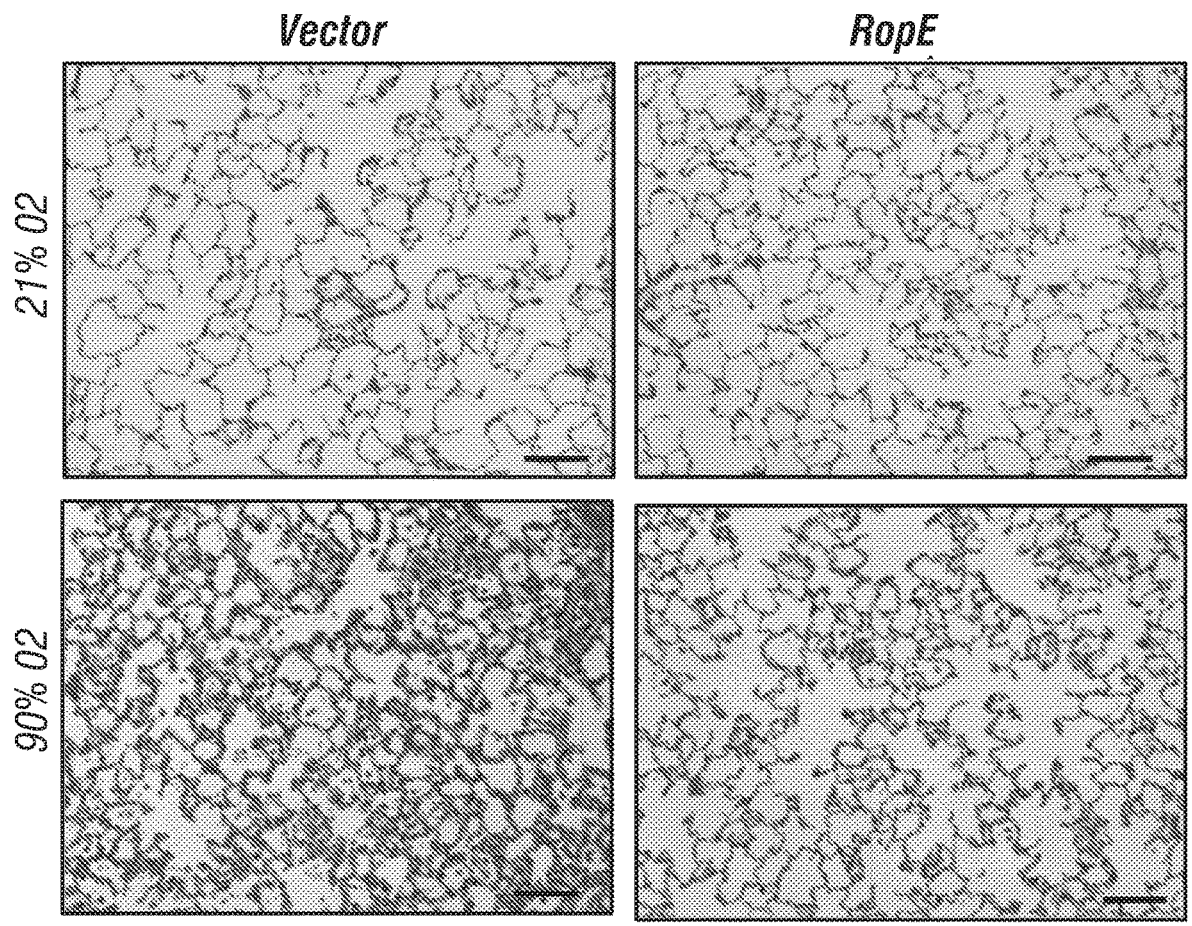

A transcriptome analysis was performed to compare gene expression profiles in post-PNX canine lung tissue versus human lung epithelial cells (A549) over-expressing RopE. Over lapping upregulated genes included cytokines, ECM proteins, adhesion molecules, and families of zinc-finger proteins. Endogenous RopE was found to be increased during kidney injury (acute kidney injury, AM, or unilateral nephrectomy, UNX) in rats or during post-pneumonectomy (PNX) compensatory lung growth in canines. Endogenous RopE expression is increased during two types of lung injury in rates including (FIG. 3B) direct lung injury from 90% oxygen for 3 days and (FIG. 3C) indirect lung injury caused by acute ischemia-reperfusion kidney injury.

It was found that in vitro addition of RopE RNA increased both EpoR and VEGF protein expression in A549 lung cells. In human lung cells, adding RopE cDNA at 95% or 21% oxygen for 24 hours showed that RopE alleviates hyperoxia-induced cell damage (lower LDH release) and apoptosis. Delivery of RopE cDNA attenuated hyperoxia-induced increases in 8-OHdG (50% vs. 81%.*\(* p<0.05; † p<0.001)), 8-isoprostane (36% vs. 101%.*†) and protein carbonyl (22% vs. 30%.*†), and attenuated the hyperoxia-induced increase in apoptosis (27% vs. 60%.*†) compared to vector controls. Hyperoxia increased endogenous total antioxidant capacity (97%* above control) and RopE cDNA delivery further enhanced the response (143%*†).

Sprague-Dawley rats (body weight ~300 g) received plasmid DNA encoding RopE (treatment) or empty vector (control) and delivered by nebulization via a tracheal cannula. Three days after inhalation, animals were exposed to hyperoxia (90% $O_2$) or normoxia (21% $O_2$) for 3 d (n=4 each). Lung tissue was harvested for histology and assays of oxidative damage to DNA damage (8-hydroxydeoxyguanosine, 8-OHdG, ng/ml), lipid (8-isoprostane, pg/ml) and protein (carbonyl, mmoles/mg), apoptosis (caspase-8 activity, nmole/hr/µg protein) and total anti-oxidant capacity (copper reducing equivalents, CRE, µM/µg protein). All experiments were done in duplicates. Results (mean±SD) were compared by two-way ANOVA. P<0.05*vs. vector at the same $O_2$; P<0.001 † vs. normoxia in the same treatment group. RopE treatment alleviated hyperoxia-induced apoptosis and oxidative damage to protein, DNA, and lipids, increased endogenous antioxidant capacity in the lung, and ameliorated pulmonary edema and exudation (FIGS. 4A-4D).

Example 2—Nanoparticle Delivery of RopE and EpoR

Cytoprotection by RopE may complement that by EpoR and have therapeutic applications in chronic lung injury or degenerative diseases. To further characterize the EpoR-RopE balance and response to DNA insults in lung cancer cells and tissue studies were performed to examine the utility of increasing RopE expression on cancer progression and ALI in vitro and in vivo. Two experimental systems were used including selected human lung cancer cell lines (e.g., A54) and primary human alveolar type-1 (AT1) cells, and an established orthotopic lung tumor model that recapitulates human non-small cell lung cancer (NSCLC) progression (Menon et al., 2014). Interventions measures EpoR and RopE expression and downstream signal transduction. The EpoR/RopE balance was manipulated by transfection (cDNA) or knockdown (CRISPR-Cas9) of EpoR or RopE, individually or in combination. The cells were then challenged with hyperoxia or x-ray irradiation to induce DNA strand breaks and accelerate tumor transformation. The EpoR, RopE, and EpoR/RopE ratios were correlated to histology and assays of proliferation, apoptosis, migration/invasion, DNA single/double strand breaks, and repair (HRR). ALI was induced in a murine model by hyperoxia (90% $O_2$) exposure, and the contribution of each protein was tested by inhalation delivery of polymeric nanoparticles containing cDNA of: 1. Empty vector, 2. EpoR only, 3. RopE only, or 4. both EpoR and RopE. Lung injury parameters were quantified by histology, lung function testing, and biomarkers of tissue damage. The prophylactic and therapeutic potentials of EpoR-RopE system were separately tested by delivering cDNA before or after induction of ALI, respectively. In the latter format, both short- and long-term effects (1 and 4 weeks after treatment, respectively) were studied.

PLGA nanoparticles were synthesized using a standard emulsion method. A 3% w/v PLGA solution was prepared in chloroform to form a primary emulsion, then added to an aqueous solution of 5% w/v polyvinyl alcohol to create double emulsion. The preparation was be sonicated and stirred (overnight room temperature) to allow the solvent to evaporate. The NPs were then recovered by ultracentrifugation and lyophilization. EpoR and RopE cDNA's were amplified and purified using commercial kits. EpoR was FLAG-tagged and RopE was hemagglutinin (HA)-tagged. For cDNA loading into NPs, 10% w/w of cDNA was dispersed in DI water with glucose (1:1 ratio) as cryoprotectant for emulsification. Control NPs were loaded with empty vector.

For inhalation delivery, mice were immobilized and the head placed inside a cone-shaped low-dead space mask connected to a rebreathing circuit and a reservoir bag containing 100% $O_2$. The appropriate cDNA NP preparation was suspended in sterile saline (maximum 50 µL), sonicated and aerosolized (2-4 µm droplets). The animal rebreathed the nebulized mixture for 10 minutes. Oxygen was bled into the system as needed. $CO_2$ level in the system was monitored.

For hyperoxic lung injury, the animals were placed in an environmental chamber and exposed to 90% $O_2$ for 3 days. Body weight was monitored daily. For testing of ALI prevention, cDNA preparations were delivered by inhalation 3 days prior to hyperoxia exposure to allow time for protein expression in the lung to increase. For testing of ALI treatment, cDNA delivery was given at the end of hyperoxia exposure; the severity of tissue damage and recovery was assessed 1 week or 4 weeks later.

At the end of treatment and exposure, the animal was deeply anesthetized (ketamine 100 mg/kg, xylazine 10 mg/kg, acepromazine 2 mg/kg by intraperitoneal injection) and mechanically ventilated via a tracheostomy. Heart rate and transcutaneous oxygen saturation was monitored via a tail cuff. Lung function was measured. Then the animal was sacrificed by an overdose injection of euthanasia solution and the lungs harvested for histology and various assays.

TABLE 1

Results of treatment with RopE cDNA.

| | Exposure | | | |
|---|---|---|---|---|
| | 21% $O_2$ | | 90% $O_2$ | |
| Treatment | Vector | RopE | Vector | RopE |
| 8-OHdG | 0.09 ± 0.01 | 0.08 ± 0.01 | 0.16 ± 0.01 † | 0.13 ± 0.01 *† |
| 8-Isoprostane | 2.67 ± 0.26 | 2.57 ± 0.20 | 5.36 ± 0.45 † | 3.50 ± 0.09 *† |
| Carbonyl | 3.01 ± 0.27 | 2.88 ± 0.25 | 3.91 ± 0.20 † | 3.53 ± 0.18 *† |
| Caspase-8 | 13.75 ± 0.38 | 13.12 ± 0.70 | 22.05 ± 1.15 † | 16.72 ± 1.05 *† |
| CRE | 9.21 ± 1.44 | 9.42 ± 0.57 | 18.11 ± 0.72 † | 22.88 ± 0.62 *† |

Figure 5:
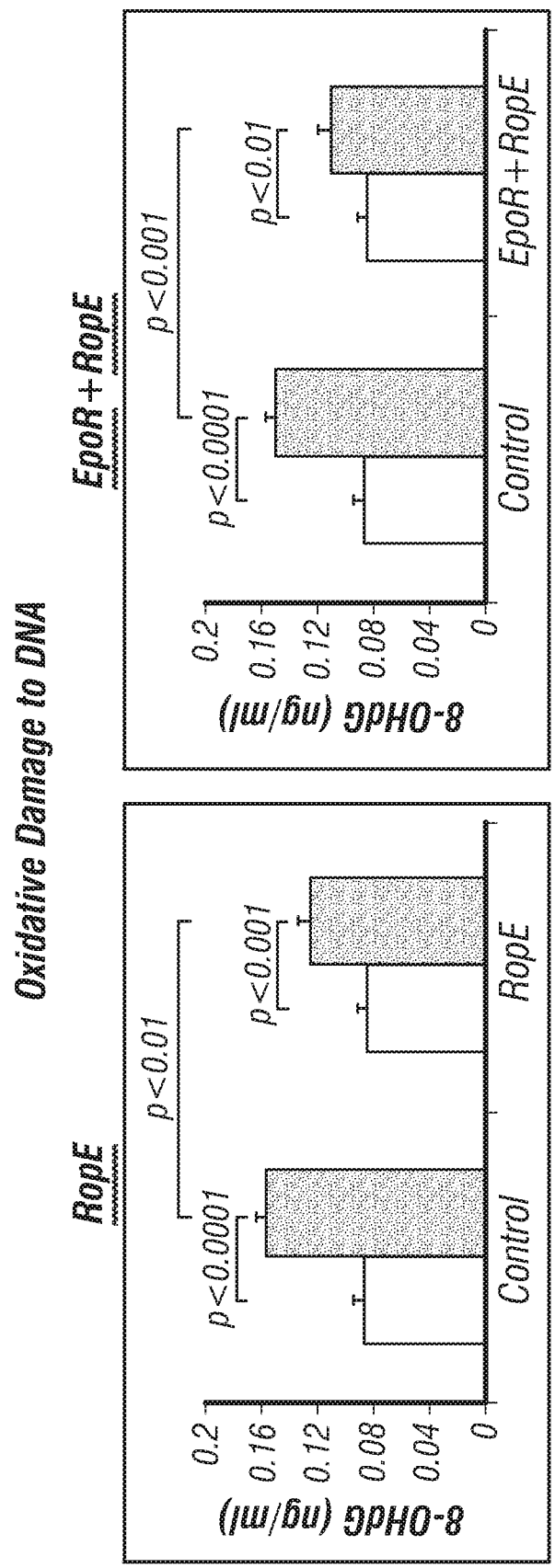
FIG. 5: Combined inhalational delivery of EpoR+RopE cDNA to the lung. Sprague Dawley rats received nebulized EpoR+RopE cDNA or vector (control) via the trachea followed by 21% or 90% $O_2$ exposure×3 days. Lung tissue was assayed for 8-OHdG as a biomarker of DNA oxidative damage. RopE delivery significantly attenuated hyperoxia-induced DNA damage; delivery of both EpoR+RopE cDNA further attenuated the increase in DNA damage compared to delivery of RopE alone, consistent with additive cytoprotective effects.
Figure 7:
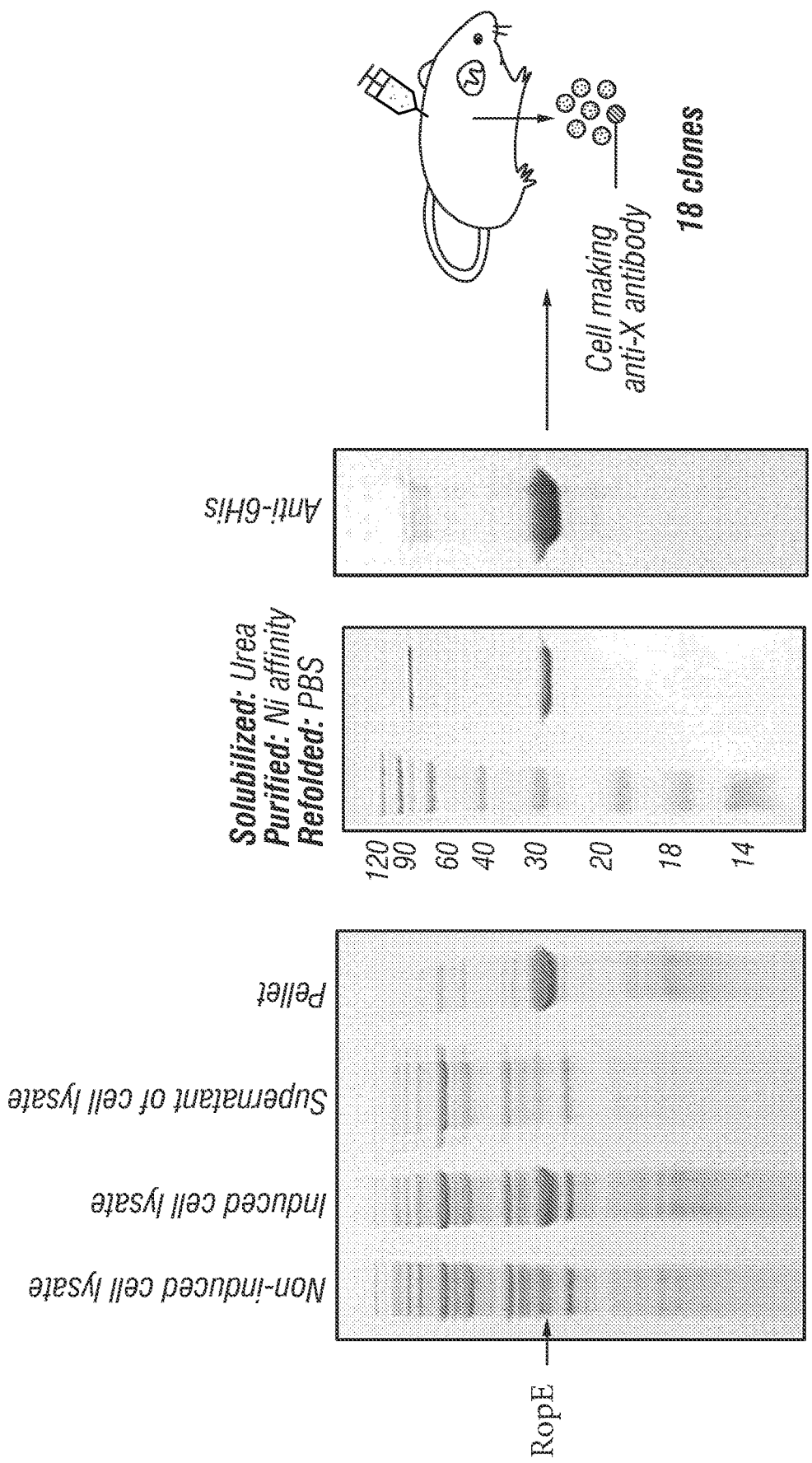
FIG. 7: Generation of MAbs to EpoR and RopE polypeptide (SEQ ID NO: 7). Peptide epitopes were selected from the predicted primary sequence in conserved regions and MAbs generated using standard protocols. Proteins were expressed in Sf9 cells with a cleavable poly-histidine affinity tag, purified, and used as immunogen for MAb production. Hybridomas were produced and screened for reactivity against and immunogens using ELISA. Positive clones were further characterized.
Figure 8A:
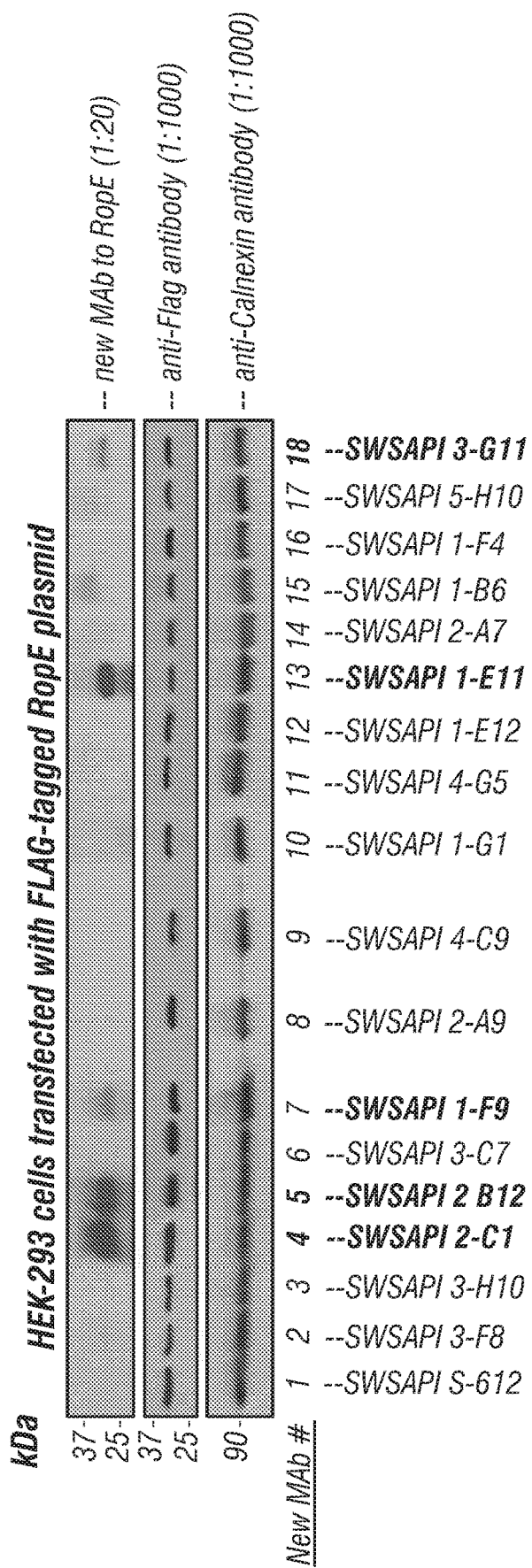
FIGS. 8A-C: Screening the new MAbs to human RopE. Human embryonic kidney-293 (HEK-293) cells were transfected with FLAG-tagged RopE plasmid and probed by each of the 18 clones of MAbs. Several clones (indicated in red) show promising labeling (FIG. 8A). The 1-E11 MAb showed specific labeling of recombinant RopE polypeptide by immunoblot (FIG. 8B), and the cells transfected with RopE cDNA by immunocytochemistry (FIG. 8C). DAPI stains the nuclei.
Figure 8B:
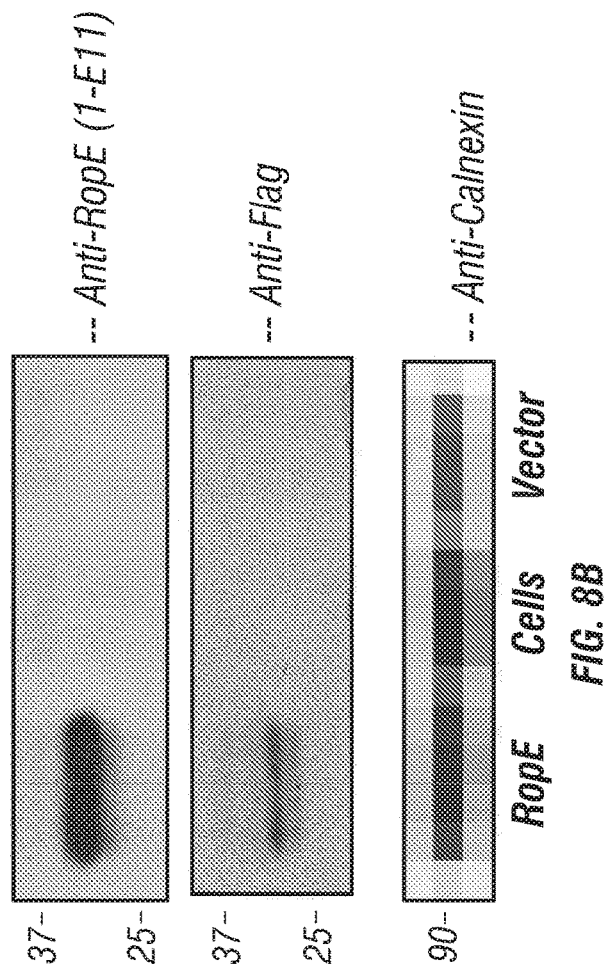
Figure 8C:
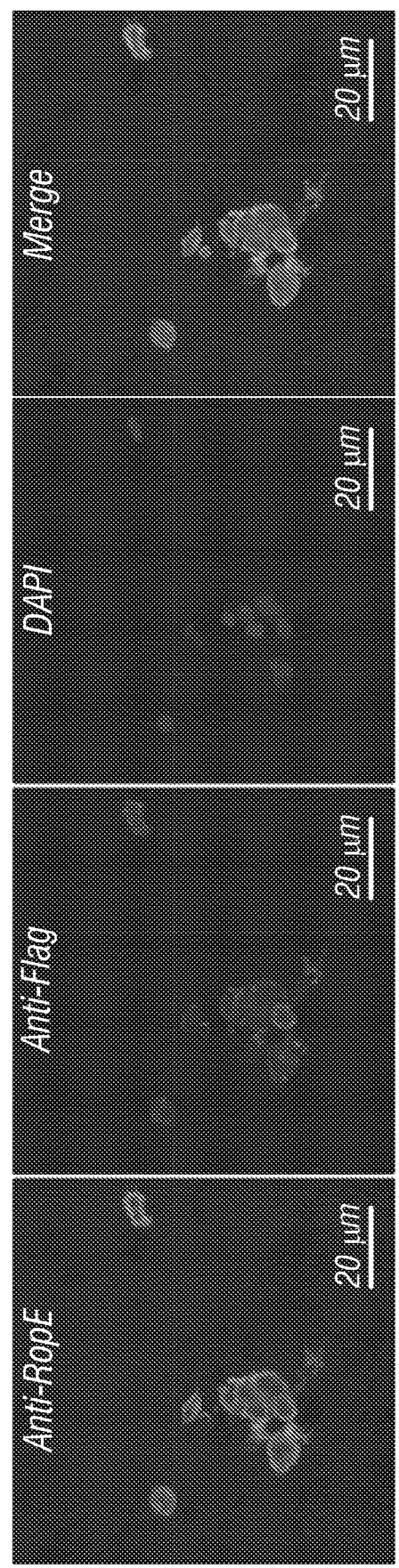

To test the effect of the combined inhalational delivery of EpoR+RopE cDNA to the lung Sprague Dawley rats received nebulized EpoR+RopE cDNA or vector (control) via the trachea followed by 21% or 90% $O_2$ exposure×3 days. Lung tissue was assayed for biomarkers of damage. Combined EpoR+RopE delivery reduced 8-OHdG more than RopE delivery alone (FIG. 5). Thus, combined delivery of EpoR and RopE protects against lung injury. RopE ameliorates acute hyperoxic injury in vivo. The protection is mediated at least partly via anti-apoptosis and increasing endogenous cellular antioxidant capacity.

Example 3—Monoclonal Antibody Development

The inventors set out to further develop and characterize monoclonal antibodies to EpoR and RopE, characterize the distribution of EpoR and RopE during normal lung development, and establish cytoprotective efficacy by the EpoR-RopE transcript system on lung cells in vitro.

Purifying RopE Peptide.

Figure 1B:
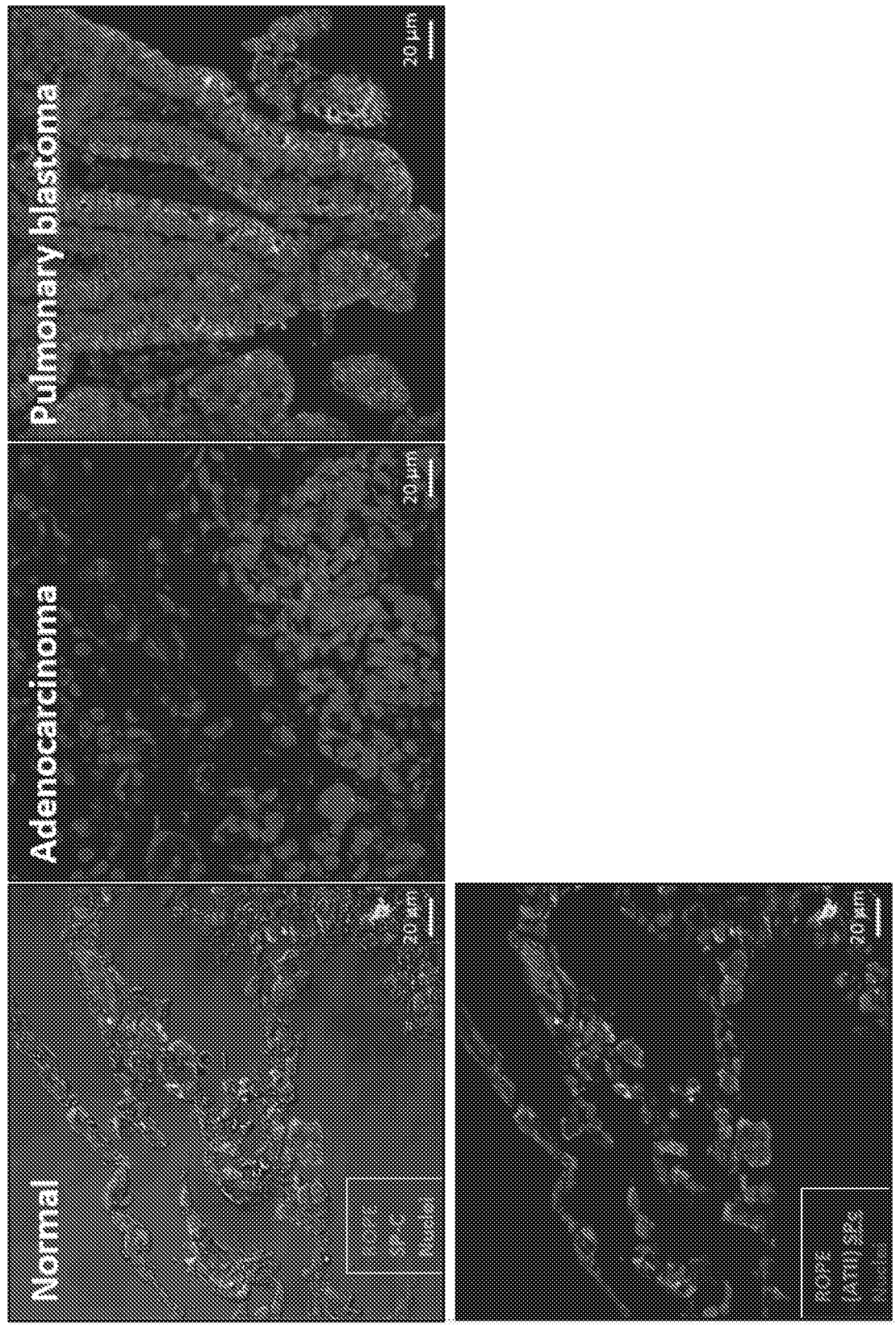
Figure 1C:
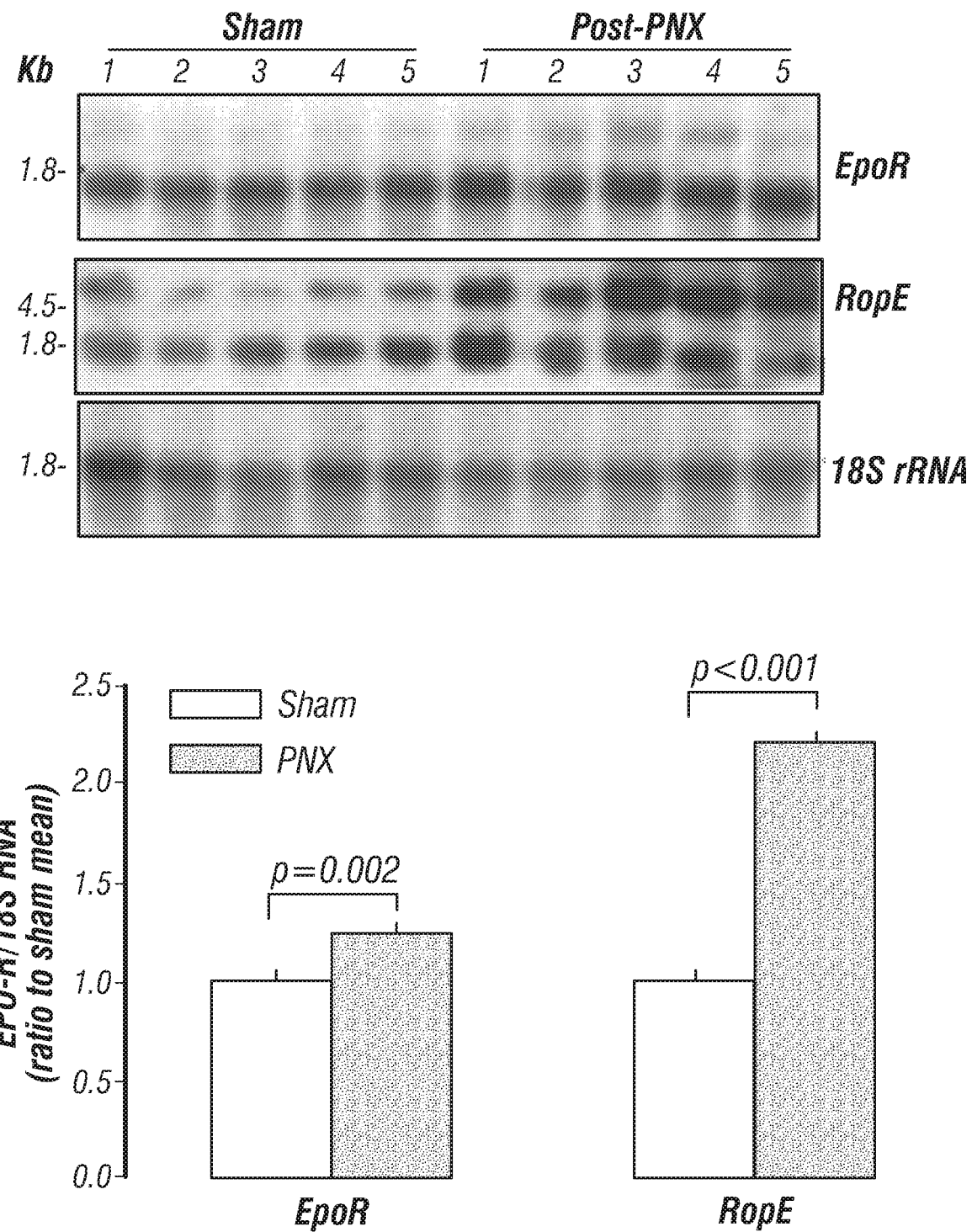
Figure 1D:
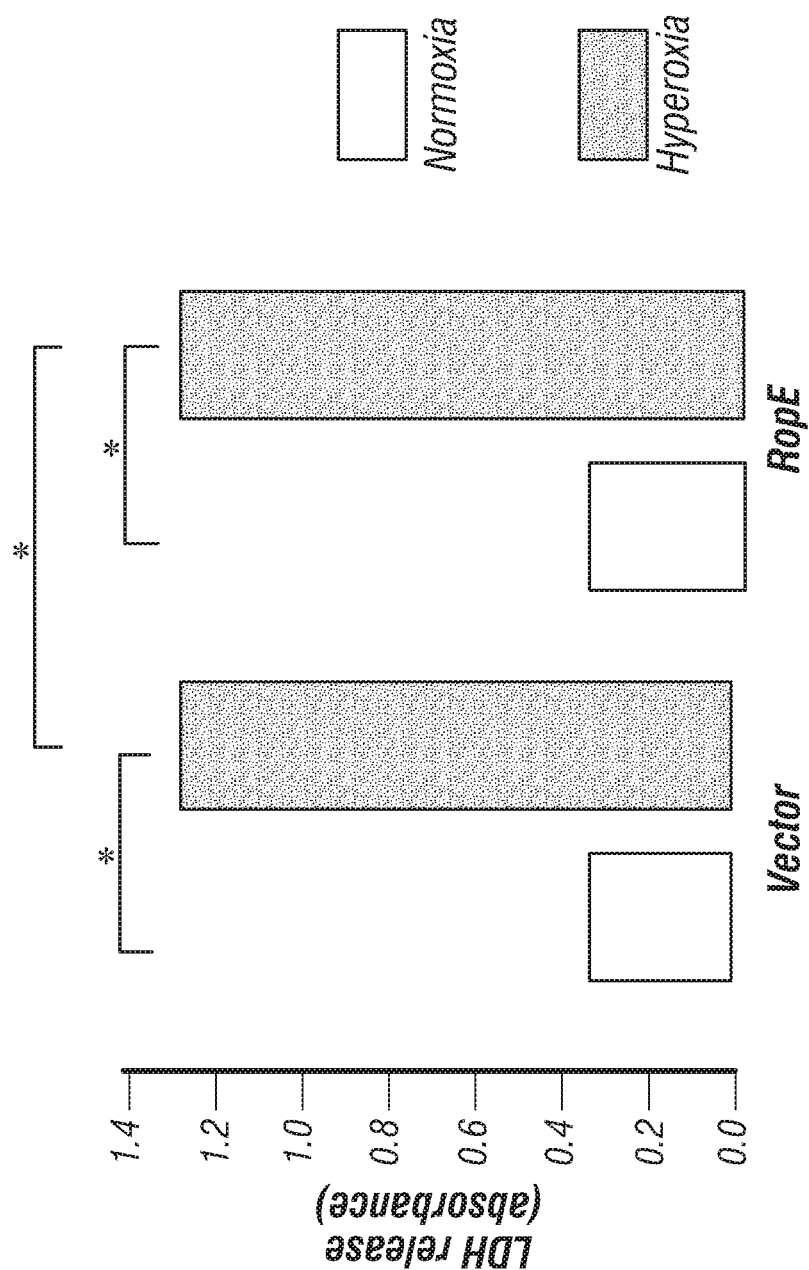
Figure 1E:
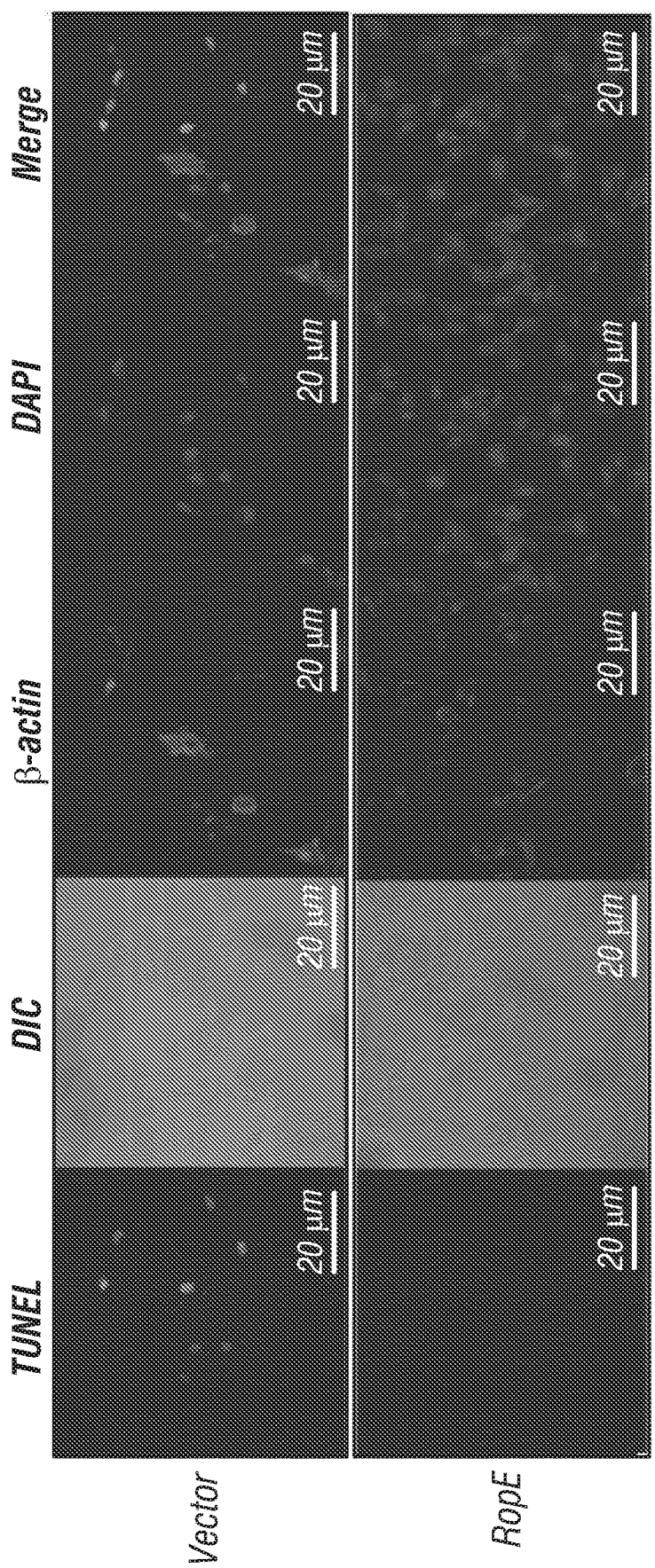

In silico analysis of the antisense EpoR (i.e., RopE) transcript revealed one open reading frame (termed ORF1) that is conserved across several mammalian species in terms of start codon, exon-intron boundary, and the primary sequence of putative translated protein (FIG. 1A). In contrast, other ORF's in the RopE transcript sequence are either very short or not conserved across species for the same parameters. In fact, ORF1 is so well conserved that it has been annotated during genome mining as a hypothetical protein (LOC61130). ORF1 predicts a cytoplasmic protein with putative ATP/GTP binding and clathrin binding motifs (FIG. 1A).

The inventors inserted epitope (FLAG) tags into the C-termini of the two antisense ORF's that codes for putative polypeptides of >10 amino acids just before the stop codons, transfected the cDNA into cells and looked for FLAG expression. Data for the two largest ORF's (ORF1 and 2) are shown. Only ORF1 gave rise to an expressed polypeptide and mutation of the start codon ATG abolished the expression (FIG. 1B). This data strongly suggests that this ORF1 is translated into an "antisense" peptide, i.e., RopE peptide.

Development of Specific Monoclonal Antibodies to EpoR and RopE Peptides.

One important obstacle hindering EpoR and RopE research is the lack of specific commercial antibodies. Of the available polyclonal anti-EpoR, only one is suitable for EpoR detection by immunoblot; none is suitable for immunohistochemistry and one recognizes mostly heat shock protein-70 instead of EpoR. These commercial EpoR antibodies revealed positive staining in tissues where EpoR mRNA was absent. None of these antibodies immunoprecipitates EpoR, and none reliably detects EpoR in tissue. The inventors previously developed a synthetic anti-EpoR in collaboration with Sachdev Sidhu (University of Toronto) which immunoprecipitates EpoR, but works poorly in immunoblots and not in immunohistochemistry applications (Hu et al., 2013). Furthermore, there is no commercial antibody to RopE, and while recombinant protein is available for EpoR the same is true of RopE. Thus, the inventors purified RopE protein, then developed monoclonal antibodies (MAbs) against human RopE (FIG. 7 and FIGS. 8A-C).

Figure 9A:
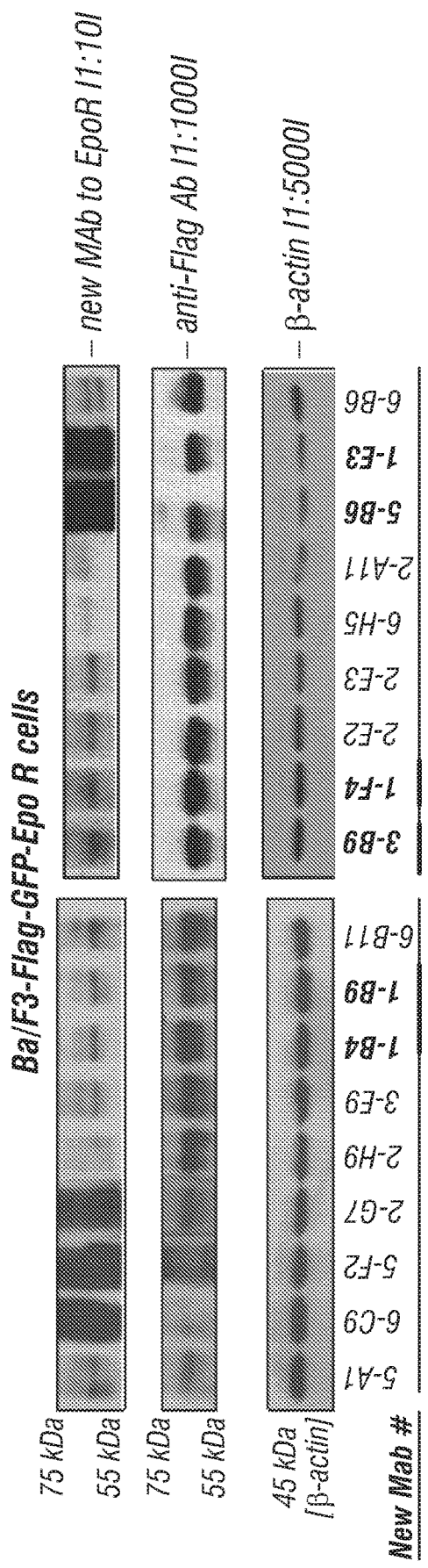
FIGS. 9A-C: Screening of new MAb clones to human EpoR. Ba/F3 cells that are naturally without EpoR expression were transfected with human EpoR cDNA, tagged Flag and GFP and used to probe each of the multiple MAb clones against human EpoR. Several clones (indicated in red) show specific labeling (FIG. 9A) and were used to probe native EpoR expression in A549 lung epithelial cells by immunoblot (FIG. 9B, #1-B9 is shown), and the Ba/F3 cells transfected with EpoR-Flag-GFP by immunocytochemistry (FIG. 9C). DAPI stains the nuclei.
Figure 9B:
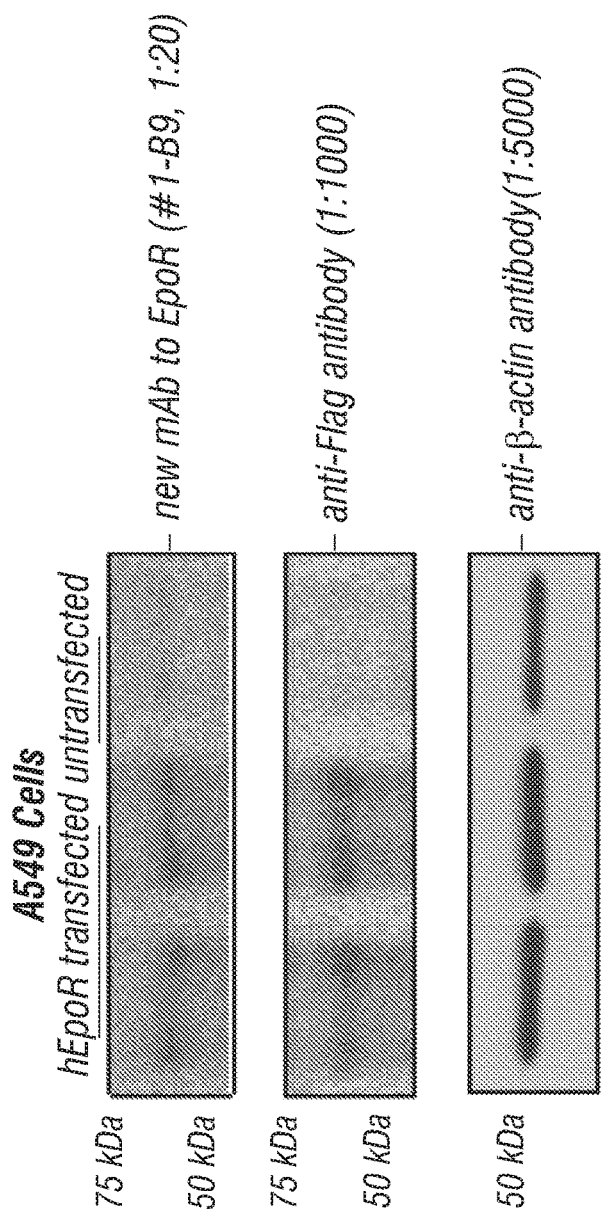
Figure 9C:
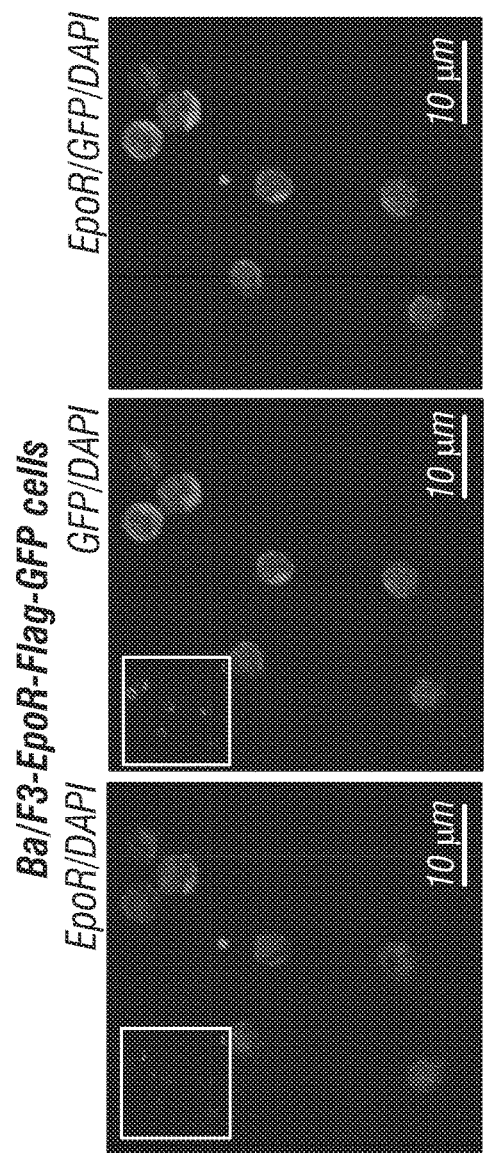
Figure 10:
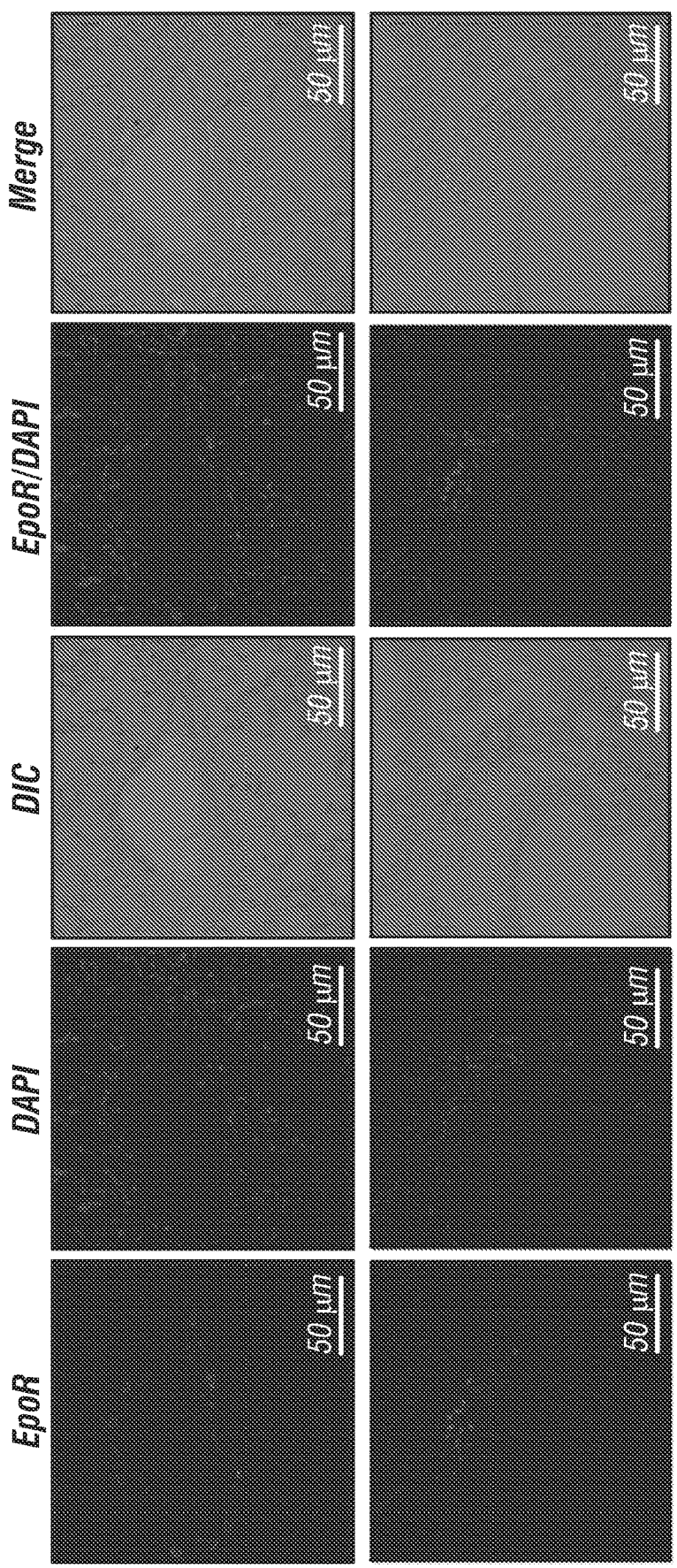
FIG. 10: Localization of EpoR expression by immunohistochemistry using the newly developed MAb in adult rat lungs fixed postmortem by tracheal instillation of 4% paraformaldehyde at a constant airway pressure (25 cm $H_2O$). EpoR expression is seen along bronchiolar walls and scattered within alveolar septa, including in cells that exhibit morphological characteristics of alveolar type 2 (AT2) epithelial cells. DAPI stains the nuclei. DIC: differential interference contrast.
Figure 10:
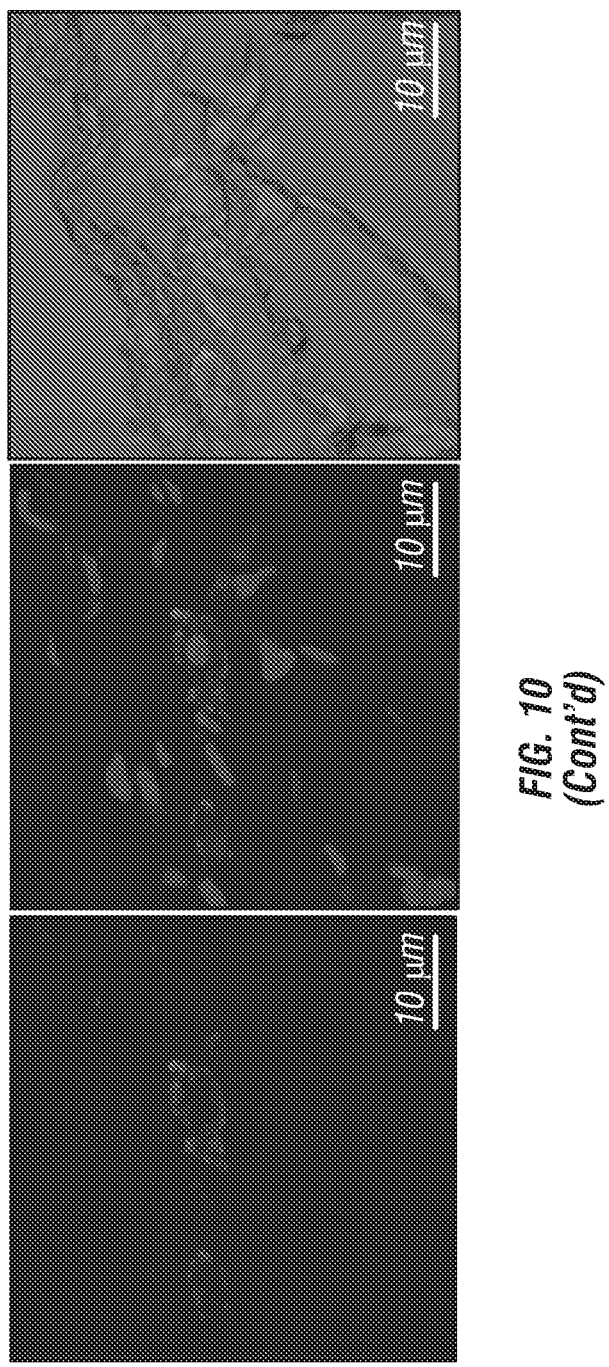
Figure 13A:
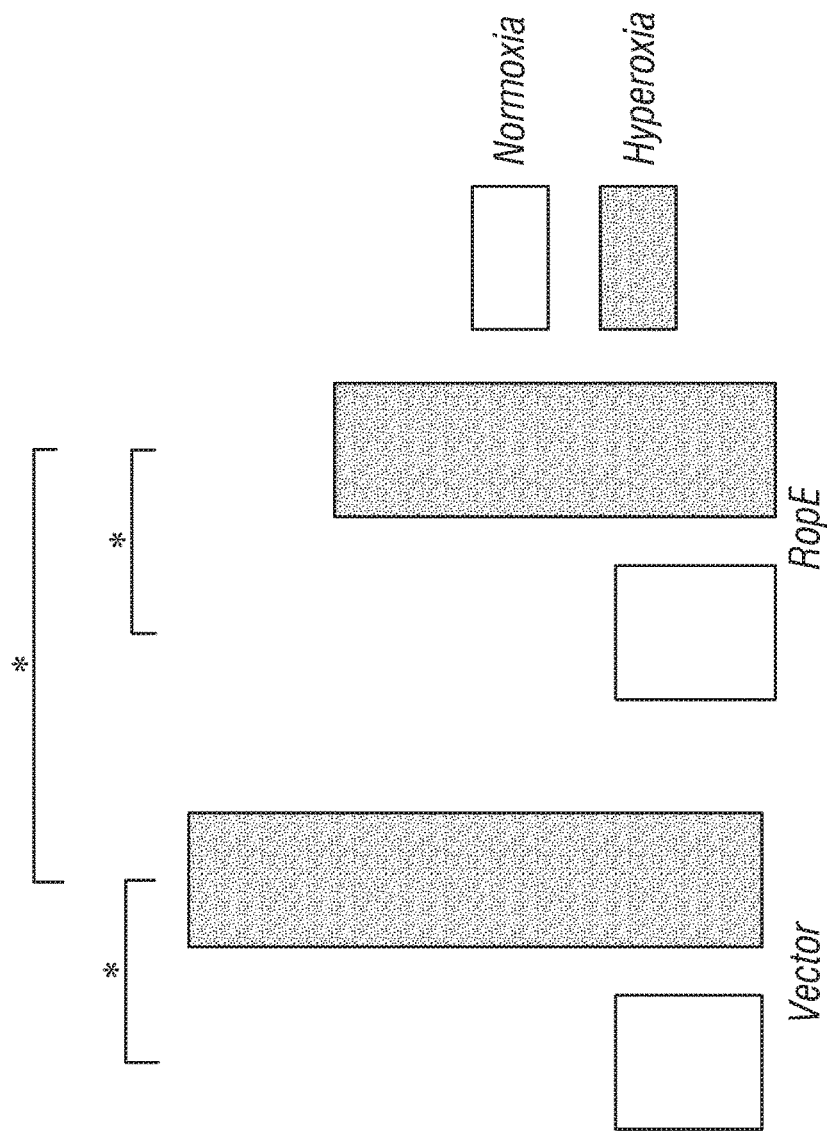
FIGS. 13A-B: RopE transfection protects lung cells against hyperoxia-induced injury. To determine the functional significance of RopE expression, A549 lung epithelial cells were transfected with RopE cDNA or vector (control), then exposed to normoxia (21% $O_2$) or hyperoxia (95% $O_2$)×24 hr. Cell death measured by lactate dehydrogenase (LDH) release (FIG. 13A) and apoptotic DNA fragmentation measured by Terminal deoxynucleotidyl transferase dUTP Nick-End Labeling (TUNEL) assay (FIG. 13B) were attenuated in RopE-treated cells. *$p<0.05$ by analysis of variance. DIC: differential interference contrast. DAPI stains the nuclei.
Figure 13B:
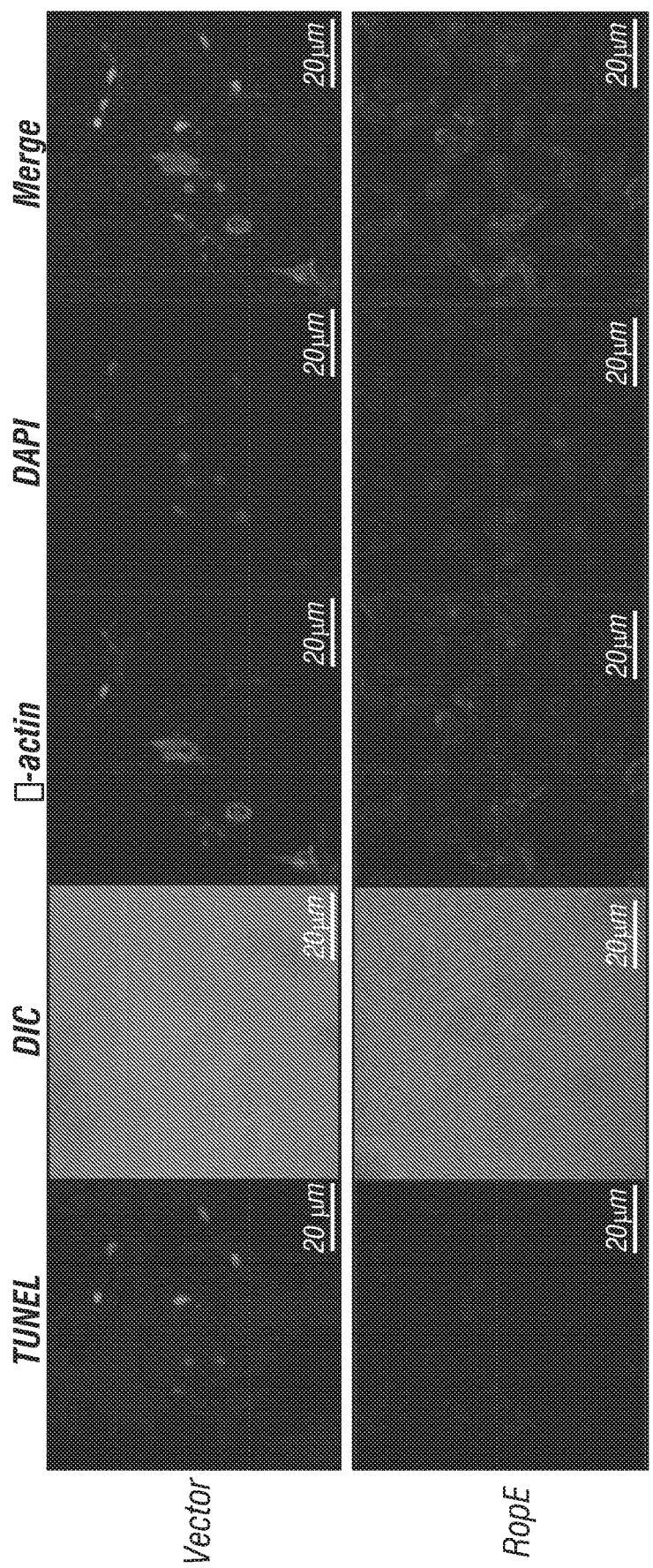
Figure 14:
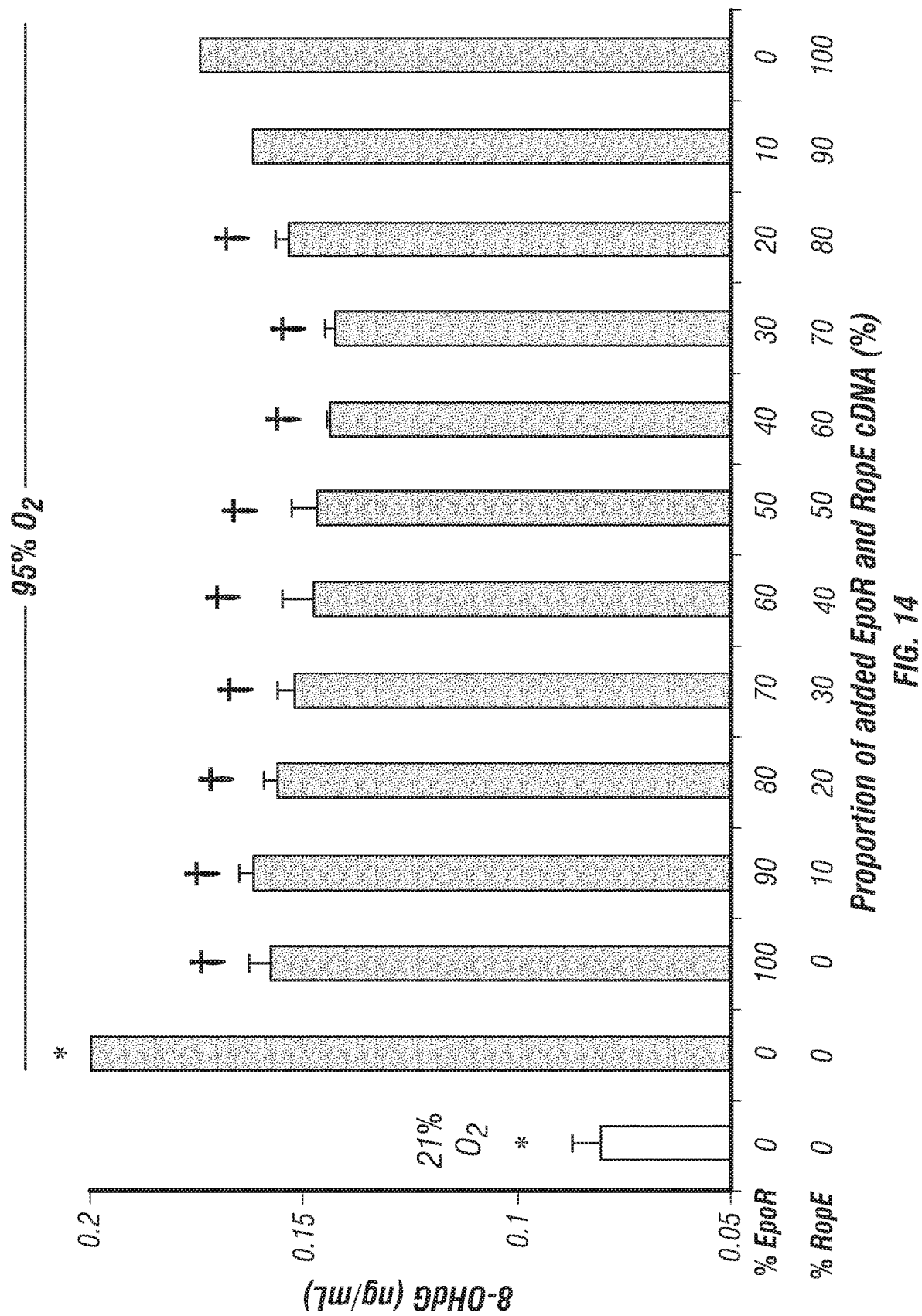
FIG. 14: Combined transfection of EpoR and RopE offers additive cytoprotection against hyperoxia-induced DNA damage in lung cells in vitro. To examine additive effects, A549 lung epithelial cells were transfected with EpoR and RopE cDNAs in different relative proportions at a fixed total (EpoR+RopE) cDNA quantity (2 µg) 24 h before being exposed to hyperoxia (95% $O_2$) for 24 hr. Control cells were exposed to hyperoxia or normoxia (21% $O_2$) without any EpoR or RopE cDNAs. Oxidative damage to DNA was measured by 8-hydroxy-2'-deoxyguanosine (8-OHdG) level. Addition of both EpoR and RopE cDNAs resulted in lower 8-OHdG levels in hyperoxia-treated cells compared to the addition of either alone. The maximum combined effect was seen at a slight RopE excess (EpoR:RopE ratio of 30%: 70%). Mean±SD of duplicate experiments. $P<0.05$: * vs. all other intervention groups; † vs. (0% EpoR, 100% RopE) by analysis of variance.

They also used commercial EpoR peptide to generate MAbs against human EpoR (FIGS. 9A-EpoR and RopE both localize to alveolar type 2 epithelial cells, which are the major resident progenitor cell in the lung (FIGS. 10-11). EpoR and RopE shown similar developmental profiles before and after birth in the lung as in the kidney; the peak expression (14 days after birth, FIG. 12) in the lung coincides with the period of lung maturation marked by the transition from the saccular to the alveolar stage. These results suggest that RopE, like EpoR, plays a role in organogenesis and maturation. Selective expression of RopE in lung cells in culture (FIG. 13) and in intact rodent lungs (FIG. 5) mitigates oxidant damage. Combined expression of both RopE and EpoR offer greater protection of lung cells from oxidant damage than either RopE or EpoR alone (FIG. 14). These results show that RopE is not just a passive byproduct of bidirectional EpoR DNA transcription; rather they support the interpretation that RopE plays a physiological role in cellular homeostasis during normal development and in adaptation to oxidative stress.

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

Azarmi et al., 60, (8), 863-75, 2008.
Brines and Cerami, *Kidney Int* 70(2):246-50, 2006.
Camacho et al., *J Clin Oncology* 22(145): Abstract No. 2505, 2004.
Chertow et al., *Arch Intern Med.* 155(14):1505-11, 1995.
Foster et al., *Am J Physiol Lung Cell Mol Physiol* 287: L1107-15, 2004.
Fults et al., *J Pharm Pharmacol* 43:726-8, 1991.
Hu et al., *Kidney Int.* 84(3):468-81, 2013.
Hurwitz et al., *Proc Natl Acad Sci USA* 95(17): 10067-10071, 1998.
International Patent Publication No. WO 98/42752
International Patent Publication No. WO2011/066342
International Patent Publication No. WO 00/37504
International Patent Publication No. WO 01/14424
International Patent Publication No. WO 02/066422
International Patent Publication No. WO 02/070490
International Patent Publication No. WO 02/076933
International Patent Publication No. WO 03/024439
International Patent Publication No. WO1995/001994
International Patent Publication No. WO2006/121168
International Patent Publication No. WO2009/101611
International Patent Publication No. WO2009/114335
International Patent Publication No. WO2010/027827
International Patent Publication No. WO2015/016718
Ku et al., *Journal of nanoscience and nanotechnology*, 8, (6), 2971-8, 2008.
Langer and Tirrell, *Nature*, 428:487-492, 2004.
Matthay et al., *J Clin Invest.* 122(8):2731-2740, 2012.
McLean et al., *Anal Chem* 72:4796-804, 2000.
Menon et al., *Journal of biomedical materials research. Part A*, 100, (8), 1998-2005, 2012.
Menon et al., *Acta biomaterialia.* 10:2643-52, 2014.
Mokyr et al., *Cancer Res* 58:5301-5304, 1998.
Murray and Lopez, *Lancet*, 349, (9064), 1498-504, 1997.
Rabe et al., *American journal of respiratory and critical care medicine*, 176, (6), 532-55, 2007.
Rees et al., *Eur J Respir Dis*, 63(Suppl): 73-78, 1982.
Sambrook et al., *Molecular Cloning: A Laboratory Manual*, 3$^{rd}$ ed., Cold Spring Harbor Press, Cold Spring Harbor, N.Y. 2001.
Sung et al., *Trends in biotechnology* 25, (12), 563-70, 2007.
Tsushima et al., *Internal medicine*, 48, (9), 621-30, 2009.
U.S. Pat. No. 4,682,195
U.S. Pat. No. 4,683,202
U.S. Pat. No. 4,870,287
U.S. Pat. No. 5,277,175
U.S. Pat. No. 5,284,133
U.S. Pat. No. 5,299,566
U.S. Pat. No. 5,355,872
U.S. Pat. No. 5,645,897
U.S. Pat. No. 5,660,166
U.S. Pat. No. 5,725,871
U.S. Pat. No. 5,756,353
U.S. Pat. No. 5,760,395
U.S. Pat. No. 5,780,045
U.S. Pat. No. 5,797,389
U.S. Pat. No. 5,804,212
U.S. Pat. No. 5,823,179
U.S. Pat. No. 5,844,905
U.S. Pat. No. 5,885,796
U.S. Pat. No. 6,016,974
U.S. Pat. No. 6,041,776
U.S. Pat. No. 6,044,841
U.S. Pat. No. 6,207,156
U.S. Pat. No. 6,241,159
U.S. Pat. No. 6,354,516
U.S. Pat. No. 6,357,671
U.S. Pat. No. 6,921,020
U.S. Pat. No. 6,926,208
U.S. Pat. No. 6,968,840
U.S. Pat. No. 6,978,941
U.S. Pat. No. 7,040,549
U.S. Pat. No. 7,083,112
U.S. Pat. No. 7,104,463
U.S. Pat. No. 7,360,536
U.S. Pat. No. 8,008,449
U.S. Pat. No. 8,119,129
U.S. Pat. No. 8,329,867
U.S. Pat. No. 8,354,509
U.S. Pat. No. 8,735,553
U.S. Patent Publication No. 2002/0020409
U.S. Patent Publication No. 2002/0020412
U.S. Patent Publication No. 2011/0008369
U.S. Patent Publication No. 2013/0315831
U.S. Patent Publication No. 2014/022021
U.S. Patent Publication No. 2014/0294898
Vecellio None et al., *J Aerosol Med* 14:107-14, 2001.
Zanen et al., *Int J Pharm*, 107:211-217, 1994.
Zanen et al., *Thorax*, 51: 977-980, 1996.
Zhang et al., *Proc Natl Acad Sci.* 105:7612-7617, 2008.

---

What is claimed is:

1. A nanoparticle comprising antisense-encoded erythropoietin receptor (RopE) protein and/or a nucleic acid encoding RopE, wherein said nanoparticle does not contain erythropoietin receptor (EpoR) protein and/or a nucleic acid encoding EpoR.

2. The nanoparticle of claim 1, wherein the nucleic acid is a messenger RNA (mRNA), a plasmid DNA (pDNA), or a complementary DNA (cDNA).

3. The nanoparticle of claim 1, wherein the nanoparticle is a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube.

4. The nanoparticle of claim 1, wherein the nanoparticle is a poly(lactic-co-glycolic) (PLGA), poly(lactic acid) (PLA), poly(glycolic acid) (PGA), or chitosan nanoparticle.

5. The nanoparticle of claim 1, wherein the nanoparticle is a lipid-polymer hybrid nanoparticle.

6. The nanoparticle of claim 1, wherein the nanoparticle is a lipid-PLGA hybrid nanoparticle.

7. The nanoparticle of claim 1, further comprising a cryoprotectant.

8. The nanoparticle of claim 1, wherein the nanoparticle has a diameter between 150 nm to 250 nm, or 100 nm to 200 nm, or 175 nm to 222 nm.

9. The nanoparticle of claim 1, further comprising an imaging agent and/or a targeting molecule.

10. A pharmaceutical composition comprising nanoparticles according to claim 1 and a pharmaceutically acceptable excipient.

11. The composition of claim 10, wherein the pharmaceutical composition is formulated for inhalation, aerosols, lung delivery, nasal delivery, airway instillation, oral administration, mucosal application, or vascular injection into a vein or artery.

12. A method for treating a lung disorder in a subject comprising administering a therapeutically effective amount of an antisense-encoded erythropoietin receptor (RopE) protein and/or a nucleic acid encoding RopE to the subject, wherein said method does not comprise administering erythropoietin receptor (EpoR) protein and/or a nucleic acid encoding EpoR.

13. The method of claim 12, wherein said RopE protein or nucleic acid is formulated in a nanoparticle.

14. The method of claim 13, wherein the nanoparticle is a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene or a nanotube.

15. The method of claim 13, wherein the nanoparticle is a poly(lactic-co-glycolic) (PLGA), poly(lactic acid) (PLA), poly(glycolic acid) (PGA), or chitosan nanoparticle.

16. The method of claim 13, wherein the nanoparticle is a lipid-polymer hybrid nanoparticle.

17. The method of claim 13, wherein the nanoparticle is a lipid-PLGA hybrid nanoparticle.

18. The method of claim 13, wherein the nanoparticle has a diameter between 150 nm to 250 nm, or 100 nm to 200 nm, or 175 nm to 222 nm.

19. The method of claim 13, wherein the nanoparticle further comprises an imaging agent and/or a targeting molecule.

20. The method of claim 12, wherein the nucleic acid is a messenger RNA (mRNA), a plasmid DNA (pDNA), or a complementary DNA (cDNA).

21. The method of claim 12, wherein administering comprises inhalation, aerosol delivery, lung delivery, nasal delivery, airway instillation, oral administration, mucosal application, or vascular injection into a vein or artery.

* * * * *

SEQUENCE LISTING

<160> NUMBER OF SEQ ID NOS: 1

<210> SEQ ID NO 1
<211> LENGTH: 227
<212> TYPE: PRT
<213> ORGANISM: Artificial sequence
<220> FEATURE:
<223> OTHER INFORMATION: Synthetic peptide

<400> SEQUENCE: 1

```
Met Pro Ala Ala Gly Pro Pro Leu Leu Leu Leu Gly Thr Pro Gly Ser
1               5                   10                  15

Gly Lys Thr Ala Leu Leu Phe Ala Ala Ala Leu Glu Ala Ala Gly Glu
            20                  25                  30

Gly Arg Gly Pro Val Leu Phe Leu Thr Arg Arg Pro Leu Gln Ser Leu
        35                  40                  45
```

```
Pro Arg Gly Thr Gly Ala Ala Leu Asp Pro Leu Arg Leu Gln Lys Ile
    50              55                  60

Arg Phe Gln Tyr Pro Pro Ser Thr His Glu Leu Leu Gln Leu Leu Cys
65              70                  75                      80

Ser Ala His Glu Ala Leu Gly Pro Ala Pro Ser Leu Leu Leu Leu Asp
            85                  90                  95

Gly Leu Glu Glu Tyr Leu Val Glu Asp Ser Gln Glu Ala Ala Tyr Leu
                100             105                 110

Ala Ala Leu Leu Leu Asp Thr Ala Ala His Phe Ser His Arg Thr Gly
            115             120             125

Pro Gly Gln Gly Cys Gly Leu Ile Val Ala Leu Gln Ile Gln Glu Glu
    130             135                 140

Glu Glu Ser Gly Asp Gly Leu Gln Leu Ser Leu Leu Gln Arg Tyr Phe
145             150             155                     160

Pro Ala Gln Cys Trp Leu Gln Val Asp Ala Pro Gly Pro Gly Gln Arg
                165             170                 175

Gly Leu Arg Ala Cys Leu Asp Ser Gly Gly Leu Ser Pro Arg Ala Glu
            180             185                 190

Trp Trp Val Ala Phe Arg Pro Asp Gly Glu Met Thr Ile Thr Pro Trp
        195             200                 205

Pro Thr Gln Ser Gly Asn Pro Asn Ser Asp Lys Gly Ser Ser Ser Gly
    210             215                 220

Gly Gln Pro
225
```